(12) United States Patent
Harris et al.

(10) Patent No.: US 8,067,563 B2
(45) Date of Patent: Nov. 29, 2011

(54) TUMOR SUPPRESSOR GENE, P47ING3

(75) Inventors: Curtis C. Harris, Garrett Park, MD (US); Makoto Nagashima, Kiryu (JP)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/724,305

(22) Filed: Mar. 15, 2010

(65) Prior Publication Data
US 2010/0323351 A1    Dec. 23, 2010

Related U.S. Application Data

(62) Division of application No. 11/962,906, filed on Dec. 21, 2007, now Pat. No. 7,709,609, which is a division of application No. 10/203,532, filed as application No. PCT/US01/04425 on Feb. 9, 2001, now Pat. No. 7,335,749.

(60) Provisional application No. 60/181,292, filed on Feb. 9, 2000.

(51) Int. Cl.
*C07H 21/04* (2006.01)
*C12N 15/00* (2006.01)

(52) U.S. Cl. ................................ 536/23.5; 435/320.1

(58) Field of Classification Search .................. None
See application file for complete search history.

(56) References Cited

U.S. PATENT DOCUMENTS

| 6,117,633 | A | 9/2000 | Garkavtsev et al. |
| 6,297,366 | B1 | 10/2001 | Gudkov et al. |
| 6,569,662 | B1 * | 5/2003 | Tang et al. ............... 435/212 |
| 2005/0048623 | A1 * | 3/2005 | Hillman et al. ............ 435/69.1 |

FOREIGN PATENT DOCUMENTS

| WO | WO 97/21809 A1 | 9/1997 |
| WO | WO 00/58473 A2 | 10/2000 |
| WO | WO 01/07471 A2 | 2/2001 |

OTHER PUBLICATIONS

U.S. Appl. No. 60/121,891, filed Feb. 26, 1999, Harris et al.
Campbell, A., "Monoclonal antibody technology: the production and characterization of rodent and human hybridomas," *Laboratory Techniques in Biochemistry and Molecular Biology* (1984(13 (1): 1-33.
Dauphin, et al., "Hypothetical protein (fragment)," XP002177545, Database Swissprot Online Entry/Acc. No. O60394, 1 page (Aug. 1, 1998).
Garkavtsev, et al., "The candidate tumour suppressor p33$^{ING1}$ cooperates with p53 cell growth control," *Nature* (Jan. 1998) 391(15): 295-298.
Garkavtsev, et al., "Suppression of the novel growth inhibitor p33$^{ING1}$ promotes neoplastic transformation," *Nature Genetics* (Dec. 1996) 14: 415-420.
Garkavtsev, et al., "Homo Sapiens Candidate Tumor Suppressor p33ING1 (ING1) mRNA," Database GenBank Online Entry/Acc. No. AF044076, 2 pages, (Feb. 4, 1998).
Green, et al., "Homo Sapiens PAC Clone RP5-872F7 from 7q31," Database GenBank Online Entry/Acc. No. AC004537, 28 pages (Feb. 3, 2000).
Invitrogen™ product information sheet for protein standards and ladders (Jan. 3, 2008) pp. 1-4.
Kultima, et al., *BMC Bioinformatics* (2006) 7:475 internet pp. 1-27.
Nagashima, et al., "DNA Damage-Inducible Gen p33ING2 Negatively Regulates Cell Proliferation Through Acetylation of p53," *PNAS*, vol. 98, No. 17, pp. 9671-9676, (Aug. 14, 2001).
Sambrook, et al., *Molecular Cloning*, 2$^{nd}$ Ed., Cold Spring Harbor Press (1989) pp. 18-47.
Saito, et al., "p24/ING1-ALT1 and p47/ING1-ALT2, Distinct Alternative Transcripts of p33/ING1," *J. Hum. Genet.*, (2000) vol. 45, Jpn Soc Hum Genet and Springer-Verlag, pp. 177-181.
Stein, et al., *Cancer Research* (Apr. 2004) 64: 2805-2816.
Strausberg, et al., "qc48c10.x1 Soares_Pregnant_Uterus_NbHPU Homo Sapiens cDNA Clone IMAGE: 1712850 3' Similar to TR:000532 000532 P33ING1. ;. mRNA Sequence." XP002177544, Database EMBL Online Entry/Acc. No. AI129337, 2 pages, (Sep. 22, 1998).
Zips, et a., In vivo (2005) 19: 1-7.

* cited by examiner

*Primary Examiner* — Laura B Goddard
(74) *Attorney, Agent, or Firm* — Kilpatrick Townsend & Stockton LLP

(57) ABSTRACT

The invention provides isolated nucleic acid and amino acid sequences of novel human tumor suppressors, antibodies to such tumor suppressors, methods of detecting such nucleic acids and proteins, methods of screening for modulators of tumor suppressors, and methods of diagnosing and treating tumors with such nucleic acids and proteins.

5 Claims, 4 Drawing Sheets

Figure 4
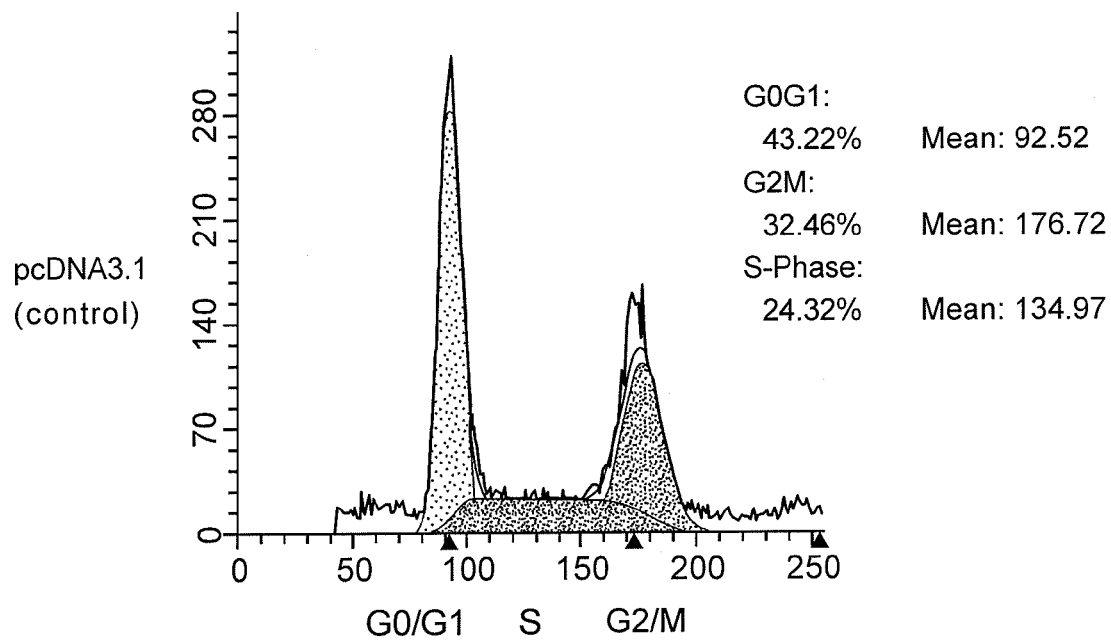
pcDNA3.1 (control)
G0G1: 43.22% Mean: 92.52
G2M: 32.46% Mean: 176.72
S-Phase: 24.32% Mean: 134.97
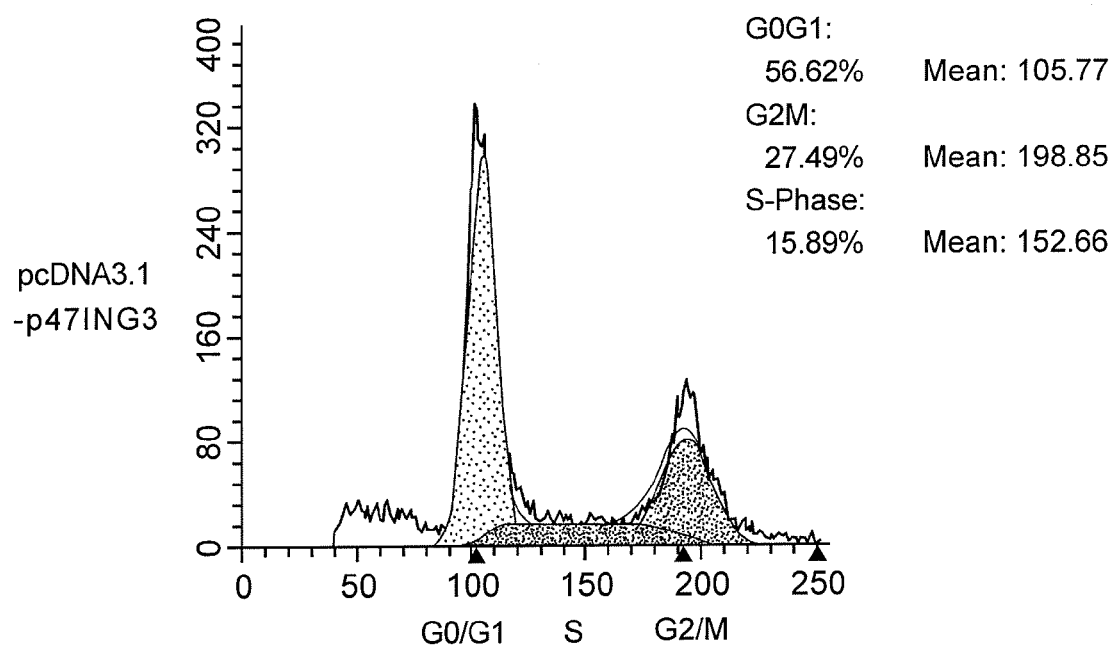
pcDNA3.1 -p47ING3
G0G1: 56.62% Mean: 105.77
G2M: 27.49% Mean: 198.85
S-Phase: 15.89% Mean: 152.66

SEQUENCE LISTING

<160> NUMBER OF SEQ ID NOS: 9

<210> SEQ ID NO 1
<211> LENGTH: 418
<212> TYPE: PRT
<213> ORGANISM: Homo sapiens
<220> FEATURE:
<223> OTHER INFORMATION: p47ING3

<400> SEQUENCE: 1

```
Met Leu Tyr Leu Glu Asp Tyr Leu Glu Met Ile Glu Gln Leu Pro Met
 1               5                  10                  15

Asp Leu Arg Asp Arg Phe Thr Glu Met Arg Glu Met Asp Leu Gln Val
                20                  25                  30

Gln Asn Ala Met Asp Gln Leu Glu Gln Arg Val Ser Glu Phe Phe Met
            35                  40                  45

Asn Ala Lys Lys Asn Lys Pro Glu Trp Arg Glu Gln Met Ala Ser
         50                  55                  60

Ile Lys Lys Asp Tyr Tyr Lys Ala Leu Glu Asp Ala Asp Glu Lys Val
 65                  70                  75                  80

Gln Leu Ala Asn Gln Ile Tyr Asp Leu Val Asp Arg His Leu Arg Lys
                85                  90                  95

Leu Asp Gln Glu Leu Ala Lys Phe Lys Met Glu Leu Glu Ala Asp Asn
            100                 105                 110

Ala Gly Ile Thr Glu Ile Leu Glu Arg Arg Ser Leu Glu Leu Asp Thr
        115                 120                 125

Pro Ser Gln Pro Val Asn Asn His Ala His Ser His Thr Pro Val
130                 135                 140

Glu Lys Arg Lys Tyr Asn Pro Thr Ser His His Thr Thr Thr Asp His
145                 150                 155                 160

Ile Pro Glu Lys Lys Phe Lys Ser Glu Ala Leu Leu Ser Thr Leu Thr
                165                 170                 175

Ser Asp Ala Ser Lys Glu Asn Thr Leu Gly Cys Arg Asn Asn Asn Ser
            180                 185                 190

Thr Ala Ser Ser Asn Asn Ala Tyr Asn Val Asn Ser Ser Gln Pro Leu
        195                 200                 205

Gly Ser Tyr Asn Ile Gly Ser Leu Ser Ser Gly Thr Gly Ala Gly Ala
    210                 215                 220

Ile Thr Met Ala Ala Ala Gln Ala Val Gln Ala Thr Ala Gln Met Lys
225                 230                 235                 240

Glu Gly Arg Arg Thr Ser Ser Leu Lys Ala Ser Tyr Glu Ala Phe Lys
                245                 250                 255

Asn Asn Asp Phe Gln Leu Gly Lys Glu Phe Ser Met Ala Arg Glu Thr
            260                 265                 270

Val Gly Tyr Ser Ser Ser Ala Leu Met Thr Thr Leu Thr Gln Asn
        275                 280                 285

Ala Ser Ser Ser Ala Ala Asp Ser Arg Ser Gly Arg Lys Ser Lys Asn
    290                 295                 300

Asn Asn Lys Ser Ser Ser Gln Gln Ser Ser Ser Ser Ser Ser Ser Ser
305                 310                 315                 320

Ser Leu Ser Ser Cys Ser Ser Ser Thr Val Val Gln Glu Ile Ser
                325                 330                 335

Gln Gln Thr Thr Val Val Pro Glu Ser Asp Ser Asn Ser Gln Val Asp
            340                 345                 350
```

```
Trp Thr Tyr Asp Pro Asn Glu Pro Arg Tyr Cys Ile Cys Asn Gln Val
        355                 360                 365

Ser Tyr Gly Glu Met Val Gly Cys Asp Asn Gln Asp Cys Pro Ile Glu
    370                 375                 380

Trp Phe His Tyr Gly Cys Val Gly Leu Thr Glu Ala Pro Lys Gly Lys
385                 390                 395                 400

Trp Tyr Cys Pro Gln Cys Thr Ala Ala Met Lys Arg Arg Gly Ser Arg
            405                 410                 415

His Lys

<210> SEQ ID NO 2
<211> LENGTH: 1807
<212> TYPE: DNA
<213> ORGANISM: Homo sapiens
<220> FEATURE:
<223> OTHER INFORMATION: p47ING3

<400> SEQUENCE: 2
agcgggtgct gctagcggag gcgccatatt ggaggggaca aaactccggc gacagcgagt      60
gacacaaata aaccccctgga ccccccttgtt ccctcagctc taagggccgc gatgttgtac    120
ctagaagact atctggaaat gattgagcag cttcctatgg atctgcggga ccgcttcacg    180
gaaatgcgcg agatggacct gcaggtcag aatgcaatgg atcaactaga acaaagagtc    240
agtgaattct ttatgaatgc aaagaaaaat aaacctgagt ggagggaaga gcaaatggca    300
tccatcaaaa aagactacta taagcttttg gaagatgcag atgagaaggt tcagttggca    360
aaccagatat atgacttggt agatcgacac ttgagaaagc tggatcagga actggctaag    420
tttaaaatgg agctggaagc tgataatgct ggaattacag aaatattaga gaggcgatct    480
ttggaattag acactccttc acagccagtg aacaatcacc atgctcattc acatactcca    540
gtggaaaaaa ggaaatataa tccaacttct caccatacga caacagatca tattcctgaa    600
aagaaattta atctgaagc tcttctatcc acccttacgt cagatgcctc taaggaaaat    660
acactaggtt gtcgaaataa taattccaca gcctcttcta acaatgccta caatgtgaat    720
tcctcccaac tctgggatc ctataacatt ggctcgttat cttcaggaac tggtgcaggg    780
gcaattacca tggcagctgc tcaagcagtt caggctacag ctcagatgaa ggagggacga    840
agaacatcaa gtttaaaagc cagttatgaa gcatttaaga ataatgactt tcagttggga    900
aaagaatttt caatggccag ggaaacagtt ggctattcat catcttcggc acttatgaca    960
acattaacac agaatgccag ttcatcagca gccgactcac ggagtggtcg aaagagcaaa   1020
aacaacaaca gtcttcaag ccagcagtca tcatcttcct cctcctcttc ttccttatca   1080
tcgtgttctt catcatcaac tgttgtacaa gaaatctctc aacaaacaac tgtagtgcca   1140
gaatctgatt caaatagtca ggttgattgg acttacgacc caaatgaacc tcgatactgc   1200
atttgtaatc aggtatctta tggtgagatg gtgggatgtg ataaccaaga ttgccctata   1260
gaatggttcc attatggctg cgttggattg acagaggcac caaaaggcaa atggtactgt   1320
ccacagtgca ctgctgcaat gaagagaaga ggcagcagac acaaataaag gtggtccttt   1380
tgtttgatga agaaataaac ttcagctgaa gattttatat aggactttaa aaagaagaga   1440
agagaaagaa gaaacaatgc atttccaggc aaccacttaa aggattttaca tagcaatcc   1500 tataagatct tgaacttgaa ttttatgggt tgtatttttaa taatgtaagt aaattattta   1560
tgcactcctg gtgtgctatg aatattattc cagttagcct tggattatttt cagtggccaa   1620 catatgcaga catttgtact cctcaaccat tttctcaaag taatgggcat tctatgattt   1680
```

```
agacttcaag gaattccaat gatgaagatt ttaaggaaag tatttatat tcaacaggta    1740 tattctgctg catgtactgt actccagagc tgttatgtaa cactgtatat aaatggttgc    1800
aaaaaaa                                                              1807
```

<210> SEQ ID NO 3
<211> LENGTH: 7
<212> TYPE: PRT
<213> ORGANISM: Homo sapiens
<220> FEATURE:
<223> OTHER INFORMATION: amino acids 1-7 of p47ING3 encoded by
      degenerate primers

<400> SEQUENCE: 3

Met Leu Tyr Leu Glu Asp Tyr
 1               5

<210> SEQ ID NO 4
<211> LENGTH: 7
<212> TYPE: PRT
<213> ORGANISM: Homo sapiens
<220> FEATURE:
<223> OTHER INFORMATION: amino acids 412-418 encoded by p47ING3
      degenerate primers

<400> SEQUENCE: 4

Arg Arg Gly Ser Arg His Lys
 1               5

<210> SEQ ID NO 5
<211> LENGTH: 17
<212> TYPE: PRT
<213> ORGANISM: Homo sapiens
<220> FEATURE:
<223> OTHER INFORMATION: peptide 141-157 of p47ING3 (ping-3)

<400> SEQUENCE: 5

His Thr Pro Val Glu Lys Arg Lys Tyr Asn Pro Thr Ser His His Thr
 1               5                  10                  15

Thr

<210> SEQ ID NO 6
<211> LENGTH: 280
<212> TYPE: PRT
<213> ORGANISM: Homo sapiens
<220> FEATURE:
<223> OTHER INFORMATION: p33ING2

<400> SEQUENCE: 6

Met Leu Gly Gln Gln Gln Gln Leu Tyr Ser Ser Ala Ala Leu Leu
 1               5                  10                  15

Thr Gly Glu Arg Ser Arg Leu Leu Thr Cys Tyr Val Gln Asp Tyr Leu
                20                  25                  30

Glu Cys Val Glu Ser Leu Pro His Asp Met Gln Arg Asn Val Ser Val
            35                  40                  45

Leu Arg Glu Leu Asp Asn Lys Tyr Gln Glu Thr Leu Lys Glu Ile Asp
         50                 55                 60

Asp Val Tyr Glu Lys Tyr Lys Lys Glu Asp Leu Asn Gln Lys Lys
 65                 70                  75                  80

Arg Leu Gln Gln Leu Leu Gln Arg Ala Leu Ile Asn Ser Gln Glu Leu
                85                  90                  95

Gly Asp Glu Lys Ile Gln Ile Val Thr Gln Met Leu Glu Leu Val Glu
            100                 105                 110

```
Asn Arg Ala Arg Gln Met Glu Leu His Ser Gln Cys Phe Gln Asp Pro
            115                 120                 125

Ala Glu Ser Glu Arg Ala Ser Asp Lys Ala Lys Met Asp Ser Ser Gln
130                 135                 140

Pro Glu Arg Ser Ser Arg Arg Pro Arg Arg Gln Arg Thr Ser Glu Ser
145                 150                 155                 160

Arg Asp Leu Cys His Met Ala Asn Gly Ile Glu Asp Cys Asp Asp Gln
                165                 170                 175

Pro Pro Lys Glu Lys Lys Ser Lys Ser Ala Lys Lys Lys Lys Arg Ser
            180                 185                 190

Lys Ala Lys Gln Glu Arg Glu Ala Ser Pro Val Glu Phe Ala Ile Asp
        195                 200                 205

Pro Asn Glu Pro Thr Tyr Cys Leu Cys Asn Gln Val Ser Tyr Gly Glu
    210                 215                 220

Met Ile Gly Cys Asp Asn Glu Gln Cys Pro Ile Glu Trp Phe His Phe
225                 230                 235                 240

Ser Cys Val Ser Leu Thr Tyr Lys Pro Lys Gly Lys Trp Tyr Cys Pro
                245                 250                 255

Lys Cys Arg Gly Asp Asn Glu Lys Thr Met Asp Lys Ser Thr Glu Lys
            260                 265                 270

Thr Lys Lys Asp Arg Arg Ser Arg
        275                 280

<210> SEQ ID NO 7
<211> LENGTH: 1080
<212> TYPE: DNA
<213> ORGANISM: Homo sapiens
<220> FEATURE:
<223> OTHER INFORMATION: p33ING2

<400> SEQUENCE: 7
gcggccgcgg ccggtgcatg tgcggctgct ggatgcggag gcggcggcga cggcgcggat      60
cggcaggatg ttagggcagc agcagcagca actgtactcg tcggctgcgc tcctgaccgg     120
ggagcggagc cggctgctca cctgctacgt gcaggactac cttgagtgcg tggagtcgct     180
gccccacgac atgcagagga acgtgtctgt gctgcgagag ctggacaaca atatcaaga     240 aacgttaaag gaaattgatg atgtctacga aaaatataag aaagaagatg atttaaacca     300
gaagaaacgt ctacagcagc ttctccagag agcactaatt aatagtcaag aattgggaga     360
tgaaaaaata cagattgtta cacaaatgct cgaattggtg aaaatcgggc aagacaaat     420 ggagttacac tcacagtgtt ccaagatcc tgctgaaagt gaacgagcct cagataaagc     480
aaagatggat ccagccaac cagaaagatc ttcaagaaga ccccgcaggc agcggaccag     540
tgaaagccgt gatttatgtc acatggcaaa tgggattgaa gactgtgatg atcagccacc     600
taaagaaaag aaatccaagt cagcaaagaa aaagaaacgc tccaaggcca agcaggaaag     660
ggaagcttca cctgttgagt ttgcaataga tcctaatgaa cctacatact gcttatgcaa     720
ccaagtgtct tatggggaga tgataggatg tgacaatgaa cagtgtccaa ttgaatggtt     780
tcacttttca tgtgtttcac ttacctataa accaaagggg aaatggtatt gcccaaagtg     840
caggggagat aatgagaaaa caatggacaa aagtactgaa aagacaaaaa aggatagaag     900
atcgaggtag taaggccat ccacatttta aagggttatt tgtctttat ataattcgtt      960 tgctttcaga aatgttttta gggtaaatgc ataagactat gcaataattt ttaatcatta    1020
gtattaatgg tgtattaaaa gttgttgtac tttgaaaaaa aaaaaaaaa aaaaaaaaa      1080
```

```
<210> SEQ ID NO 8
<211> LENGTH: 279
<212> TYPE: PRT
<213> ORGANISM: Homo sapiens
<220> FEATURE:
<223> OTHER INFORMATION: p33ING1

<400> SEQUENCE: 8

Met Leu Ser Pro Ala Asn Gly Glu Gln Leu His Leu Val Asn Tyr Val
  1               5                  10                  15

Glu Asp Tyr Leu Asp Ser Ile Glu Ser Leu Pro Phe Asp Leu Gln Arg
             20                  25                  30

Asn Val Ser Leu Met Arg Glu Ile Asp Ala Lys Tyr Gln Glu Ile Leu
         35                  40                  45

Lys Glu Leu Asp Glu Cys Tyr Glu Arg Phe Ser Arg Glu Thr Asp Gly
     50                  55                  60

Ala Gln Lys Arg Met Leu His Cys Val Gln Arg Ala Leu Ile Arg
 65                  70                  75                  80

Ser Gln Glu Leu Gly Asp Glu Lys Ile Gln Ile Val Ser Gln Met Val
                 85                  90                  95

Glu Leu Val Glu Asn Arg Thr Arg Gln Val Asp Ser His Val Glu Leu
            100                 105                 110

Phe Glu Ala Gln Gln Glu Leu Gly Asp Thr Ala Gly Asn Ser Gly Lys
        115                 120                 125

Ala Gly Ala Asp Arg Pro Lys Gly Glu Ala Ala Gln Ala Asp Lys
    130                 135                 140

Pro Asn Ser Lys Arg Ser Arg Arg Gln Arg Asn Asn Glu Asn Arg Glu
145                 150                 155                 160

Asn Ala Ser Ser Asn His Asp His Asp Asp Gly Ala Ser Gly Thr Pro
                165                 170                 175

Lys Glu Lys Lys Ala Lys Thr Ser Lys Lys Lys Arg Ser Lys Ala
            180                 185                 190

Lys Ala Glu Arg Glu Ala Ser Pro Ala Asp Leu Pro Ile Asp Pro Asn
        195                 200                 205

Glu Pro Thr Tyr Cys Leu Cys Asn Gln Val Ser Tyr Gly Glu Met Ile
    210                 215                 220

Gly Cys Asp Asn Asp Glu Cys Pro Ile Glu Trp Phe His Phe Ser Cys
225                 230                 235                 240

Val Gly Leu Asn His Lys Pro Lys Gly Lys Trp Tyr Cys Pro Lys Cys
                245                 250                 255

Arg Gly Glu Asn Glu Lys Thr Met Asp Lys Ala Leu Gly Lys Ser Lys
            260                 265                 270

Lys Glu Arg Ala Tyr Asn Arg
        275

<210> SEQ ID NO 9
<211> LENGTH: 10
<212> TYPE: PRT
<213> ORGANISM: Homo sapiens
<220> FEATURE:
<223> OTHER INFORMATION: peptide 1-10 of p47ING3 (Ping-3N peptide)

<400> SEQUENCE: 9

Met Leu Tyr Leu Glu Asp Tyr Leu Glu Met
  1               5                  10
```

TUMOR SUPPRESSOR GENE, P47ING3

CROSS-REFERENCES TO RELATED APPLICATIONS

This application is a divisional of U.S. application Ser. No. 11/962,906 filed Dec. 21, 2007, now U.S. Pat. No. 7,709,609, which is a divisional of U.S. application Ser. No. 10/203,532 filed Aug. 8, 2002, now U.S. Pat. No. 7,335,749, which is a National Stage application of PCT/US01/04425 filed Feb. 9, 2001, which claims benefit of U.S. provisional application No. 60/181,292 filed Feb. 9, 2000. Each application is herein incorporated by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to isolated nucleic acid and amino acid sequences of novel human tumor suppressors, antibodies to such tumor suppressors, methods of detecting such nucleic acids and proteins, methods of screening for modulators of tumor suppressors, and methods of diagnosing and treating tumors with such nucleic acids and proteins.

BACKGROUND OF THE INVENTION

Certain tumors, benign, premalignant, and malignant, are known to have genetic components. Mutations or inactivation of "tumor suppressor" genes causes some of these tumors. In normal cells, the tumor suppressor genes are involved in the regulation of cell growth and proliferation and in the control of cellular aging, anchorage dependence and apoptosis. When the tumor suppressor genes are mutated or inactivated, cells are transformed and become immortalized or tumorigenic. These transformed cells can be reverted back to the normal phenotype (i.e., the cell growth rate is suppressed) by introducing the wildtype suppressor genes.

The first tumor suppressor gene identified was the nuclear phosphoprotein, retinoblastoma gene (Rb). Retinoblastoma is a malignant tumor of the sensory layer of the retina, and often occurs bilaterally during childhood. Retinoblastoma exhibits a familial tendency, but it can be acquired. Mutations in the Rb gene and inactivation of its product have been shown to be involved in other tumors, such as bladder, breast, and small cell lung carcinomas, osteosarcomas, and soft tissue sarcomas. It was demonstrated that reconstitution of Rb-deficient tumor cells with the wildtype Rb leads to the suppression of growth rate or tumorigenicity (Huang et al., *Science* 242:1563-1566 (1988)). This result provides direct evidence that Rb protein is a tumor suppressor.

Another well-characterized tumor suppressor is the gene for the nuclear phosphoprotein, p53. More than half of all human cancers are associated with mutations in the tumor suppressor gene p53 (see, e.g., Hollstein et al., *Science* 253: 49-53 (1991); Caron de Fronmentel & Soussi, *Genes Chromosom. Cancer* 4: 1-15; Harris & Hollstein, *N. Engl. J. Med.* 329:1318-1327 (1993); Greenblatt et al., *Cancer Res.* 54:4855-4878 (1994)). Mutations in p53 often appear to be a critical step in the pathogenesis and progression of tumors. For example, missense mutations of p53 occur in tumors of the colon, lung, breast, ovary, bladder, and several other organs. Alternatively, inactivation of the wildtype p53 proteins in cells can cause tumors. For example, certain strains of human papillomavirus (HPV) are known to interfere with the p53 protein function, because the virus produces a protein, E6, which promotes the degradation of the p53 protein.

Recently, another tumor suppressor gene, p33ING1, has been identified. p33ING1 directly cooperates with tumor suppressor gene p53 in growth regulation (Garkavtsev et al., *Nature Genetics* 14:415-420 (1996); Garkavtsev et al., *Nature* 391:295-298 (1998); GenBank Accession No. AF044076; SEQ ID NO: 8). Neither of the two genes can alone cause growth inhibition when the other one is suppressed (Garkavtsev et al. (1998), supra). According to immunoprecipitation studies, p33ING1 proteins modulate the p53 activity through physical interaction. It has been also reported that some neuroblastoma cells have a mutation of the p33ING1 gene, and some breast cancer cell lines exhibit reduced expression of p33ING1 (Garkavtsev et al. (1996), supra). A tumor suppressor gene with homology to p33ING1, p33ING2, has also been cloned and characterized (See Harris and Nagashima, U.S. Provisional Patent Application No. 60/121,891, filed on Feb. 26, 1999; SEQ ID NOS: 6 and 7).

Cancer remains a major public concern. Although epidemiological and cytogenetic studies demonstrated that a number of recessive genetic mutations are involved in various cancers, only a limited number of tumor suppressors have been identified. Therefore, there is a need to identify and isolate other tumor suppressor genes. The identification and isolation of new tumor suppressor genes would allow aid in diagnosis, prevention, and treatment of tumors and cancers.

SUMMARY OF THE INVENTION

The present invention provides a method for identifying a compound that modulates p47ING3, the method comprising the steps of: (i) contacting the compound with a eukaryotic host cell or cell membrane in which has been expressed a tumor suppressor polypeptide (p47ING3), the polypeptide: (a) having greater than about 70% amino acid sequence identity to a polypeptide having a sequence of SEQ ID NO:1; and, (b) selectively binding to polyclonal antibodies generated against SEQ ID NO:1; and (ii) determining the functional effect of the compound upon the cell or cell membrane expressing the polypeptide.

In one embodiment, the functional effect is determined by measuring changes in cell growth.

In another aspect, the present invention provides a method of inhibiting cellular proliferation, the method comprising transducing a cell with an expression vector, the vector comprising a nucleic acid encoding a tumor suppressor polypeptide (p47ING3), the polypeptide: (i) having greater than about 70% amino acid sequence identity to a polypeptide having a sequence of SEQ ID NO:1; and, (ii) selectively binding to polyclonal antibodies generated against SEQ ID NO:1.

In another aspect, the present invention provides a method of detecting the presence or absence of p47ING3 in tumorigenic mammalian tissue, the method comprising the steps of: (i) isolating a tumorigenic sample; (ii) contacting the tumorigenic sample with a p47ING3-specific reagent that selectively associates with p47ING3; and (iii) detecting the level of p47ING3-specific reagent that selectively associates with the tumorigenic sample.

In one embodiment, the p47ING3-specific reagent is selected from the group consisting of a p47ING3-specific antibody, a p47ING3-specific primer; and a p47ING3-specific nucleic acid probe.

In another aspect, the present invention provides a for an isolated nucleic acid encoding a tumor suppressor polypeptide (p47ING3), the nucleic acid comprising the nucleic acid sequence of SEQ ID NO: 2.

Also, the present invention provides an expression vector comprising the nucleic acid of SEQ ID NO: 2. In one embodiment, a host cell is transfected with an expression vector comprising the nucleic acid of SEQ ID NO:2.

In another aspect, the present invention provides an isolated tumor suppressor polypeptide (p47ING3), the polypeptide comprising an amino acid sequence of SEQ ID NO: 1.

The present invention further provides an antibody that selectively binds to a p47ING3 polypeptide of SEQ ID NO: 1. In one embodiment, the antibody is polyclonal.

BRIEF DESCRIPTION OF THE DRAWINGS

FIG. 4 shows a FACS analysis of the RKO (human colon carcinoma) cells transfected with pcDNA3.1 (top panel) or pcDNA3.1-p47ING3 (bottom panel). The cells were co-transfected with the plasmid pEGFP-F. The cells were stained with propidium iodide. The cells were then gated for GFP fluorescence using FACscan.

DETAILED DESCRIPTION OF THE INVENTION

I. Introduction

Figure 1:
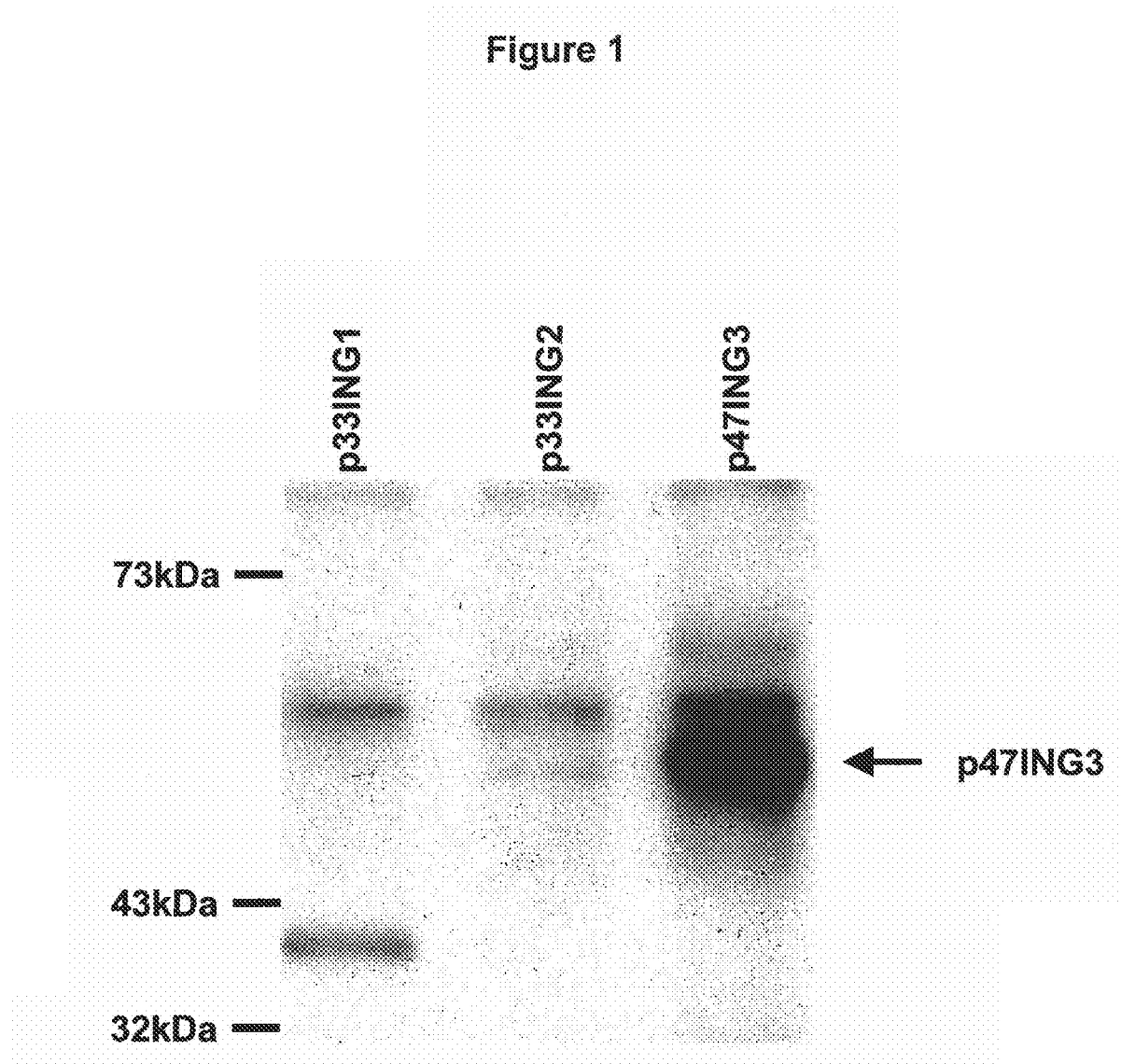
FIG. 1 illustrates binding specificities of polyclonal antibodies for p47ING3 raised against SEQ ID NO: 5 by Western blot analysis. The molecular sizes of standards are indicated in kDa on the left hand border of the gel. The proteins were produced using the TNT T7 Quick Coupled Transcription/Translation System, Cat. #L1170 from Promega Corporation of Madison, Wis.

The present invention provides for the first time nucleic acids and polypeptides of a new tumor suppressor called p47ING3. The present invention also provides antibodies which specifically hybridize to a p47ING3 protein. These nucleic acids and the polypeptides they encode are tumor suppressors that are involved in the regulation of cell proliferation and in the control of cellular aging, anchorage dependence, and apoptosis.

The present invention also provides methods of screening for modulators (e.g., activators, inhibitors, stimulators, enhancers, agonists, and antagonists) of these novel p47ING3 proteins. Such modulators are useful for pharmacological and genetic modulation of cell growth and tumor suppression. The invention thus provides assays for tumor suppression and cell growth, where p47ING3 acts as a direct or indirect reporter molecule for measuring the effect of modulators on cell growth or tumor suppression. These assays can measure various parameters that are affected by the p47ING3 activity, e.g., cell growth on soft agar, contact inhibition and density limitation of growth, growth factor or serum dependence, tumor specific markers levels, invasiveness into Matrigel, tumor growth in vivo, arrest of cells in $G_0/G_1$ phase of the cell-cycle, p47ING3 protein or mRNA levels, transcriptional activation or repression of a reporter gene, and the like.

The present invention also provides methods of inhibiting cell proliferation of a cell by transducing the cell with an expression vector containing p47ING3 nucleic acids. The transduced cell may have a missense or null endogenous p47ING3 phenotype or a mutation in another tumor suppressor gene. Expression of wildtype p47ING3 restores cell growth regulation and prevents the development of tumor. For example, p47ING3 nucleic acids can be used to treat cancer or other cell proliferative diseases, such as hyperplasia, in patients.

Finally, the invention provides for methods of detecting p47ING3 or nucleic acid and protein expression, allowing investigation of cell growth regulation and tumor suppression. Furthermore, p47ING3 nucleic acid and protein expression can be used to diagnose cancer in patients who have a defect in one or more copies of p47ING3 in their genome.

Functionally, p47ING3 represents a protein having a molecular weight of approximately 40-47 kDa. It is involved in the regulation of cell proliferation and in the control of cellular aging, anchorage and apoptosis.

Structurally, the nucleotide sequence of p47ING3 (see, e.g., SEQ ID NO:2, isolated from a human) encodes a polypeptide of approximately 418 amino acids with a predicted molecular weight of approximately 47 kDa (see, e.g., SEQ ID NO:1). Related p47ING3 genes from other species share at least about 70% amino acid identity over an amino acid region of at least about 25 amino acids in length, preferably 50 to 100 amino acids in length.

Specific regions of the p47ING3 nucleotide and amino acid sequences may be used to identify polymorphic variants, interspecies homologs, and alleles of p47ING3. This identification can be made in vitro, e.g., under stringent hybridization conditions or with PCR and sequencing, or by using the sequence information in a computer system for comparison with other nucleotide or amino acid sequences. Typically, identification of polymorphic variants and alleles of p47ING3 is made by comparing an amino acid sequence of about 25 amino acids or more, preferably 50-100 amino acids. Amino acid identity of approximately at least 70% or above, preferably 80%, most preferably 90-95% or above typically demonstrates that a protein is a polymorphic variant, interspecies homolog, or allele of p47ING3. Sequence comparison can be performed using any of the sequence comparison algorithms discussed below. Antibodies that bind specifically to p47ING3 or a conserved region thereof can also be used to identify alleles, interspecies homologs, and polymorphic variants.

Polymorphic variants, interspecies homologs, and alleles of p47ING3 are confirmed by examining the effect of putative p47ING3 expression on cell growth and tumor suppression using the methods and assays described herein. Typically, p47ING3 having the amino acid sequence of SEQ ID NO: 1 is used as a positive control. For example, immunoassays using antibodies directed against the amino acid sequence of SEQ ED NOS: 1, 5, or 9 can be used to demonstrate the identification of a polymorphic variant or allele of p47ING3. Alternatively, p47ING3 having the nucleic acid sequences of SEQ ID NO:2 is used as a positive control, e.g., in in situ hybridization with SEQ ID NO:2 to demonstrate the identification of a polymorphic variant or allele of p47ING3. The polymorphic variants, alleles and interspecies homologs of p47ING3 are expected to retain the ability to inhibit cell proliferation and tumor suppression. These functional characteristics can be tested using various assays, such as soft agar assay, contact inhibition and density limitation of growth assay, growth factor or serum dependence assay, tumor specific markers assay, invasiveness assay, tumor growth assay, etc.

p47ING3 nucleotide and amino acid sequence information may also be used to construct models of tumor suppressor polypeptides in a computer system. These models are subsequently used to identify compounds that can activate or inhibit p47ING3. Such compounds that modulate the activity of p47ING3 can be used to investigate the role of p47ING3 in inhibition of cell proliferation and tumor suppression or can be used as therapeutics.

Isolation of p47ING3 provides a means for assaying for modulators of p47ING3. p47ING3 is useful for testing modulators using in vivo and in vitro expression that measure various parameters, e.g., cell growth on soft agar, contact inhibition and density limitation of growth, growth factor or serum dependence, tumor specific markers levels, invasiveness into Matrigel, tumor growth in vivo, p47ING3 protein or mRNA levels, transcriptional activation or repression of a reporter gene, and the like. Such modulators identified using p47ING3 can be used to study cell growth regulation and tumor suppression, and further to treat cancer.

Methods of detecting p47ING3 nucleic acids and expression of p47ING3 are also useful for to diagnose various cancers or tumors by using assays such as northern blotting, dot blotting, in situ hybridization, RNase protection, and the like. Chromosome localization of the genes encoding human p47ING3 can also be used to identify diseases, mutations, and traits caused by and associated with p47ING3. Techniques, such as high density oligonucleotide arrays (GeneChip™, Affymetrix), can be also be used to screen for mutations, polymorphic variants, alleles and interspecies homologs of p47ING3.

II. Definitions

As used herein, the following terms have the meanings ascribed to them unless specified otherwise.

The term "tumor suppressor" refers to a gene, or the protein it encodes, that in its wildtype form has the ability to suppress, prevent, or decrease cell transformation. Tumor suppressor genes are genes that encode protein(s) that regulate cell growth and proliferation directly or indirectly, e.g., p53, Rb, and the like. If a tumor suppressor gene is damaged (e.g., by radiation, a carcinogen or inherited, or spontaneous mutation), it may lose its wildtype ability to regulate cell growth and proliferation, and the cells may become transformed or pre-disposed to transformation.

"p47ING" refers to a family of tumor suppressor nucleic acids or polypeptides having a molecular weight of approximately 40-47 kDa. They encode a nuclear protein which is involved in the regulation of cell growth and proliferation and in the control of cellular aging, anchorage and apoptosis.

The term "p47ING3" therefore refers to polymorphic variants, alleles, interspecies homologs, and mutants that: (1) have about 70% amino acid sequence identity, preferably about 80-90% amino acid sequence identity to SEQ ID NO:1 over a window of about at least 50-100 amino acids; (2) binds to polyclonal antibodies raised against an immunogen comprising an amino acid sequence selected from the group consisting of SEQ ID NO:1 and conservatively modified variants thereof, but does not bind to polyclonal antibodies raised against an immunogen comprising an amino acid sequence selected from the group consisting of SEQ ID NO:8 or SEQ ID NO: 6 and conservatively modified variants thereof; (3) specifically hybridize (with a size of at least about 500, preferably at least about 900 nucleotides) under stringent hybridization conditions to a sequence selected from the group consisting of SEQ ID NO:2, and conservatively modified variants thereof; or (4) are amplified by primers that specifically hybridize under stringent conditions to the same sequence as a degenerate primers sets encoding SEQ ID NOS:3 and 4.

A "test compound is able to modulate a p47ING3 activity" if the test compound can increase or decrease a property associated with p47ING3.

A "cell expresses p47ING3 above basal levels" when the cell produces p47ING3 protein or mRNA in amounts greater than amounts produced in the parent cell or the untransfected cell. The amount of p47ING3 protein or mRNA can be determined using methods known in the art, such as Western blots or Northern blots, respectively.

The term "modulate" refers to an increase or decrease in a parameter that is being measured.

A "p47ING3 activity" can include, but is not limited to p47ING3 mediated cell-cycle arrest, p47ING3 induced change in cell growth, p47ING3 mediated decrease of colony formation. These properties can be assayed by comparing the effect of the test compound on a cell that does not express p47ING3 above basal levels with a cell that does express p47ING3 above basal levels. Examples of assays include, but are not limited to soft agar assay, cell cycle arrest assay, colony formation assay, contact inhibition and density limitation of growth assay, growth factor or serum dependence assay, anchorage dependence assay, tumor specific markers assay, invasiveness assay, tumor growth assay, p47ING3 protein and mRNA level assays, transcriptional activation or repression of a reporter gene assay, and the like, in vitro, in vivo, and ex vivo.

A "test compound" can essentially be any compound, such as a chemotherapeutic, a peptide, a hormone, a nucleic acid and the like. The phrases "polymorphic variant" and "allele" refer to forms of p47ING3 that occur in a population (or among populations) and that maintain wildtype p47ING3 activity as measured using one of the assays described herein.

The term "mutant" of p47ING3 refers to those mutants which are experimentally made or those which are found in tumor or cancer cells. Mutants of p47ING3 can be due to, e.g., truncation, elongation, substitution of amino acids, deletion, insertion, or lack of expression (e.g., due to promoter or splice site mutations, etc.). A mutant has activity that differs from the activity of wildtype p47ING3 by at least about 20% as measured using an assay described herein. For example, a mutant of p47ING3 can have a null mutation which results in absence of normal gene product at the molecular level or an absence of function at the phenotypic level. Another example is a missense mutation of p47ING3, where a substitution of amino acid(s) results in a change in the activity of the protein.

The phrase "missense or null endogenous p47ING3 phenotype" of a cell therefore refers to p47ING3 has a missense or null mutation so that the cell has a phenotype (e.g., soft agar growth, contact inhibition and density limitation of growth, etc.) which differs from a cell having a wildtype p47ING3.

"p33ING2" and "p33ING1" are members of the "p33ING" family, which members are encoded by different genes (i.e., mapped to different regions on the chromosome). p33ING2 is mapped to human chromosome 7q31.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "transfect" or "transduce" refers to any way of getting a nucleic acid across a cell membrane, including electroporation, biolistics, injection, plasmid transfection, lipofection, viral transduction, lipid-nucleic acid complexes, naked DNA, etc A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect, amphibian, or mammalian cells such as CHO, HeLa, HCT116, RK0 cells, and the like.

"Tumorigenic sample" as used herein is a sample of biological tissue or fluid that contains nucleic acids or polypeptides of p47ING3. The biological tissue comprises cancer cells, transformed cells, a tumor, a tumor cell and the like. The fluid comprises a solution obtained from an animal comprising cancer cells, transformed cells, a tumor, tumor cells and the like. Such samples include, but are not limited to, tissue isolated from humans, mice, and rats. Tumorigenic samples may also include sections of tissues such as frozen sections taken from histological purposes. A tumorigenic sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans.

"Tumor cell" refers to precancerous, cancerous, and normal cells in a tumor.

"Cancer cells", "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, and/or malignancy (see, Freshney, *Culture of Animal Cells a Manual of Basic Technique* ($3^{rd}$ ed. 1994)).

"Inhibitors," "activators," and "modulators" of p47ING3 refer to inhibitory, activating, or modulatory molecules identified using in vitro and in vivo assays for tumor suppression, e.g., ligands, agonists, antagonists, and their homologs and mimetics. Inhibitors are compounds that decrease, block, prevent, delay activation, inactivate, desensitize, or down regulate tumor suppression, e.g., antagonists. Activators are compounds that increase, activate, facilitate, enhance activation, sensitize or up regulate tumor suppression, e.g., agonists. Modulators are inhibitors and activators and include genetically modified versions of p47ING3, e.g., with altered activity, as well as naturally occurring and synthetic ligands, antagonists, agonists, small chemical molecules and the like.

Such assays for modulators include, e.g., expressing p47ING3 in cells, applying putative modulator compounds, and then determining the functional effects on inhibition of cell proliferation or tumor suppression. Compounds identified by these assays are used to modulate tumor suppression effect of p47ING3.

Samples or assays comprising p47ING3 that are treated with a potential modulator are compared to control samples without the inhibitor, activator, or modulator. Control samples (untreated with inhibitors) are assigned a relative p47ING3 activity value of 100%. Inhibition of p47ING3 is achieved when the p47ING3 activity value relative to the control is about 90%, preferably 50%, more preferably 25-0%. Activation of p47ING3 is achieved when the p47ING3 activity value relative to the control (untreated with activators) is 110%, more preferably 150%, more preferably 200-500%, more preferably 1000-3000% higher.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique*, $3^{rd}$ ed. (Wiley-Liss, Inc. 1994), pp. 231-241, herein incorporated by reference.

The team "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radiolabel into the peptide, and used to detect antibodies specifically reactive with the peptide).

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated p47ING3 nucleic acid is separated from open reading frames that flank the p47ING3 gene and encode proteins other than p47ING3. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides (i.e., 70% identity) that are the same, when compared and aligned for maximum correspondence over a comparison window, as measured using one of the following sequence comparison algorithms or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nucleic Acids Res.* 12:387-395 (1984)).

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptides per se or the polypeptides encoded by the nucleic acids (testers) are immunologically cross reactive with the antibodies raised against the polypeptide (control) as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a Northern or Southern blot. Alternatively, another indication that the sequences are substantially identical is if the same set of PCR primers can be used to amplify both sequences.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH$_1$ by a disulfide bond. The F(ab)'2 may be reduced under mild conditions to break the disulfide linkage in the hinge region, thereby converting the F(ab)'2 dimer into an Fab' monomer. The Fab' monomer is essentially an Fab with part of the hinge region (see *Fundamental Immunology* (Paul ed., 3$^{rd}$ ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies or those synthesized de novo using recombinant DNA methodologies (e.g., single chain Fv).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

An "anti-p47ING3" antibody is an antibody or antibody fragment that specifically binds a polypeptide encoded by the p47ING3 gene, cDNA, or a subsequence thereof.

An "anti-p33ING2" antibody is an antibody or antibody fragment that specifically binds a polypeptide encoded by the p33ING2 gene, cDNA, or a subsequence thereof.

An "anti-p33ING1" antibody is an antibody or antibody fragment that specifically binds to a polypeptide encoded by the p33ING1 gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to p47ING3 at least two times the background, more typically 10 to 100 times background, and do not substantially bind in a significant amount to other proteins present in the sample. Specific binding to a polyclonal antibody under such conditions may require an antibody that is selected for its specificity for a particular protein. For example, polyclonal antibodies raised to p47ING3 from a species such as rat, mouse, or human can be selected to obtain only those polyclonal antibodies that are specifically immunoreactive with p47ING3 and not with other proteins, such as p33ING1 or p33ING2, except for polymorphic variants and alleles of p47ING3. This selection may be achieved for polyclonal antibodies by subtracting out antibodies that cross react with p33ING1 or p33ING2. For monoclonal antibodies, the specificity may be achieved by using a p47ING3 specific antigen to make the hybridomas (e.g., SEQ ID NO: 5 or SEQ ID NO: 9). For identifying p47ING3 variants and alleles from a particular species such as a human, the selection may be achieved by subtracting out antibodies that cross-react with p33ING2 or p33ING1 molecules, respectively, from other species. For species specific monoclonal antibodies, a species specific antigen can be used to make the hybridomas. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "selectively associates with" refers to the ability of a nucleic acid to "selectively hybridize" with another as defined above, or the ability of an antibody to "selectively (or specifically) bind to a protein, as defined above.

"p47ING3-specific reagent" refers to any reagent which specifically associates with p47ING3. For example, it can be a p47ING3-specific antibody, a p47ING3-specific primer, or a p47ING3-specific nucleic acid probe.

III. Isolation of the Gene Encoding p47ING3

A. General Recombinant DNA Methods p47ING3 polypeptides and nucleic acids are used in the assays described below. For example, recombinant p47ING3 can be used to make cells that constitutively express p47ING3. Such polypeptides and nucleic acids can be made using routine techniques in the field of recombinant genetics. Basic texts disclosing the general methods of use in this invention include Sambrook et al., *Molecular Cloning, A Laboratory Manual* (2$^{nd}$ ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is typically by either native acrylamide gel electrophoresis or by anion-exchange HPLC as described in Pearson & Reanier, *J. Chrom.* 255:137-149 (1983). The sequence of the cloned genes and synthetic oligonucleotides can be verified after cloning using, e.g., the chain termination method for sequencing double-stranded templates of Wallace et al., *Gene* 16:21-26 (1981). Again, as noted above, companies such as Operon Technologies, Inc. provide an inexpensive commercial source for essentially any oligonucleotide.

B. Cloning Methods for the Isolation of Nucleotide Sequences Encoding p47ING3

In general, the nucleic acid sequences encoding genes of interest, such as p47ING3 and related nucleic acid sequence homologs, are cloned from cDNA and genomic DNA libraries by hybridization with a probe, or isolated using amplification techniques with oligonucleotide primers. Preferably mammalian, more preferably human sequences are used. For example, p47ING3 sequences are typically isolated from mammalian nucleic acid (genomic or cDNA) libraries by hybridizing with a nucleic acid probe, the sequence of which can be derived from SEQ ID NO:2 A suitable tissue from which human p47ING3 RNA and cDNA can be isolated is, e.g., placenta, heart, brain, placenta, lung, liver, skeletal muscle, kidney, pancreas, spleen, thyroid, prostate, testis, ovary, small intestine, colon, peripheral blood cell, leukocyte. Heart, Brain, placenta, lung, liver, skeletal muscle, kidney, pancreas, spleen, thyroid, prostate, testis, ovary, small intestine, colon, peripheral blood cell, leukocyte Amplification techniques using primers can also be used to amplify and isolate, e.g., a nucleic acid encoding p47ING3, from DNA or RNA (see, e.g., Dieffenbach & Dveksler, *PCR Primer: A Laboratory Manual* (1995)). These primers can be used, e.g., to amplify either the full length sequence or a probe of one to several hundred nucleotides, which is then used to screen a mammalian library for the full-length nucleic acid of choice. For example, degenerate primer sets for p47ING3 sequences such as MLYLEDY (SEQ ID NO:3) and RRG-SRHK (SEQ ID NO:4) can be used to isolate p47ING3 nucleic acids. Nucleic acids can also be isolated from expression libraries using antibodies as probes. Such polyclonal or monoclonal antibodies can be raised, e.g., using the sequence of p47ING3.

Polymorphic variants and alleles that are substantially identical to the gene of choice can be isolated using nucleic acid probes, and oligonucleotides under stringent hybridization conditions, by screening libraries. Alternatively, expression libraries can be used to clone, e.g., p47ING3 and p47ING3 polymorphic variants, interspecies homologs, and alleles, by detecting expressed homologs immunologically with antisera or purified antibodies made against p47ING3, which also recognize and selectively bind to the p47ING3 homolog.

To make a cDNA library, one should choose a source that is rich in the mRNA of choice, e.g., for human p47ING3 mRNA, human colon carcinoma cell line RKO. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in non-lambda expression vectors. These vectors are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.,* 72:3961-3965 (1975).

An alternative method of isolating a nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of, e.g., p47ING3 directly from mRNA, from cDNA, from genomic libraries or cDNA libraries. Degenerate oligonucleotides can be designed to amplify p47ING3 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of p47ING3 encoding mRNA in physiological samples, for nucleic acid sequencing, or for other purposes. Genes amplified by the PCR reaction can be purified from agarose gels and cloned into an appropriate vector.

As described above, gene expression of p47ING3 can also be analyzed by techniques known in the art, e.g., reverse transcription and PCR amplification of mRNA, isolation of total RNA or poly A+ RNA, northern blotting, dot blotting, in situ hybridization, RNase protection, probing high density oligonucleotides, and the like. All of these techniques are standard in the art.

Synthetic oligonucleotides can be used to construct recombinant genes for use as probes or for expression of protein. This method is performed using a series of overlapping oligonucleotides usually 40-120 by in length, representing both the sense and non-sense strands of the gene. These DNA fragments are then annealed, ligated and cloned. Alternatively, amplification techniques can be used with precise primers to amplify a specific subsequence of the p47ING3 nucleic acid. The specific subsequence is then ligated into an expression vector.

The nucleic acid encoding the protein of choice is typically cloned into intermediate vectors before transformation into prokaryotic or eukaryotic cells for replication and/or expression. These intermediate vectors are typically prokaryote vectors, e.g., plasmids, or shuttle vectors. Optionally, cells can be transfected with recombinant p47ING3 operably linked to a constitutive promoter, to provide higher levels of p47ING3 expression in cultured cells.

C. Expression in Prokaryotes and Eukaryotes

To obtain high level expression of a cloned gene or nucleic acid, such as those cDNAs encoding p47ING3, one typically subclones p47ING3 into an expression vector that contains a strong promoter to direct transcription, a transcription/translation terminator, and if for a nucleic acid encoding a protein, a ribosome binding site for translational initiation.

1. Prokaryotic Expression

Suitable bacterial promoters are well known in the art and described, e.g., in Sambrook et al. and Ausubel et al. Bacterial expression systems for expressing the p47ING3 protein are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known in the art and are also commercially available.

2. Eukaryotic Expression

A variety of methods are known in the art for expressing a gene in eukaryotes (Ausubel et al.). These methods often achieve expression of a gene above basal.

a. Transfection of Cells with an Expression Cassette.

Cells can be transfected with an expression cassette containing the gene of interest and a promoter. The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically cam also include elements that are responsive to transactivation, e.g., hypoxia responsive elements, Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding p47ING3, and signals required for efficient polyadenylation of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a p47ING3 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the p47ING3 protein, which is recovered from the culture using standard techniques identified below.

b. Gene Activation

The method of gene activation can also be used to express an endogenous gene, e.g. p47ING3, above basal levels in a cell. Details of this technology can be found in U.S. Pat. Nos. 5,272,071, 5,641,670, EP 0747485B1, EP 0505500B1). Instead of transfecting an exogenous gene in an expression cassette into a cell, these methods rely on the introduction of nucleotide sequences into a cell that will activate the endogenous gene. The nucleotide sequences are homologously recombined into the cell's genome and cause an increase in the transcription of the endogenous gene.

One method involves the activation of a gene that is usually transcriptionally silent in the genome of a eukaryotic cell line (U.S. Pat. No. 5,641,670). Briefly, the method involves introducing a polynucleotide sequence containing a targeting sequence, a regulatory sequence, an exon, and an unpaired splice donor site. The polynucleotide sequence is introduced into the cell and homologously recombined with the endogenous gene. The homologous recombination event permits the polynucleotide sequence to be operably linked with the endogenous gene. The regulatory sequence is able to promote the transcription of the normally silent endogenous gene and expression of the gene is achieved above basal levels.

The regulatory sequence can contain one or more promoters. A variety of promoters can be used, such as sequences that regulated the expression of viral genes, actin genes, immunoglobulin genes and the like. The regulatory sequences can contain binding sites for transcription factors, which serve to promote transcription of the gene that is operably linked to the polynucleotide sequence.

IV. Purification of p47ING3

If necessary, naturally occurring or recombinant proteins can be purified for use in functional assays, e.g., to make antibodies to detect p47ING3. Naturally occurring p47ING3 can be purified, e.g., from mammalian tissue such as heart, brain, placenta, lung, liver, skeletal muscle, kidney, pancreas, spleen, thyroid, prostate, testis, ovary, small intestine, colon, peripheral blood cells, and leukocytes.

Recombinant p47ING3 is purified from any suitable expression system, e.g., by expressing p47ING3 in *E. coli* and then purifying the recombinant protein via affinity purification, e.g., by using antibodies that recognize a specific epitope on the protein or on part of the fusion protein, or by using glutathione affinity gel, which binds to GST. In some embodiments, the recombinant protein is a fusion protein, e.g., with GST or Gal4 at the N-terminus.

The protein of choice may be purified to substantial purity by standard techniques, including selective precipitation with such substances as ammonium sulfate; column chromatography, immunopurification methods, and others (see, e.g., Scopes, *Protein Purification Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversibly fused to p47ING3. With the appropriate ligand, p47ING3 can be selectively adsorbed to a purification column and then freed from the column in a relatively pure form. The fused protein is then removed by enzymatic activity. Finally, p47ING3 could be purified using immunoaffinity columns.

A. Purification of p47ING3 from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The protein of choice is separated from other bacterial proteins by standard separation techniques, e.g., with Ni-NTA agarose resin.

Alternatively, it is possible to purify the recombinant p47ING3 protein from bacteria periplasm. After lysis of the bacteria, when the protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying p47ING3

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein, e.g., p47ING3, can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein of choice can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of p47ING3

In addition to the detection of p47ING3 genes and gene expression using nucleic acid hybridization technology, one can also use immunoassays to detect p47ING3, e.g., to identify alleles, mutants, polymorphic variants and interspecies homologs of p47ING3. Immunoassays can be used to qualitatively or quantitatively analyze p47ING3, e.g., to detect p47ING3, to measure p47ING3 activity, or to identify modulators of p47ING3 activity. A general overview of the applicable technology can be found in Harlow and Lane, *Antibodies: A Laboratory Manual* (1988).

A. Antibodies to p47ING3

Methods of producing polyclonal and monoclonal antibodies that react specifically with p47ING3 are known to those of skill in the art (see, e.g., Coligan, *Current Protocols in Immunology* (1991); Harlow & Lane, supra; Goding, *Monoclonal Antibodies: Principles and Practice* (2nd ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). In addition, as noted above, many companies, such as BMA Biomedicals, Ltd., HTI Bioproducts, and the like, provide the commercial service of making an antibody to essentially any peptide.

A number of p47ING3 comprising immunogens may be used to produce antibodies specifically reactive with p47ING3. For example, recombinant p47ING3, or antigenic fragments thereof, are isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. To improve reproducibility, an inbred strain of mice (e.g., BALB/C mice) can be immunized to make the antibody; however, standard animals (mice, rabbits, etc.) used to make antibodies are immunized with the protein using a standard adjuvant, such as Freund's adjuvant, and a standard immunization protocol (see Harlow & Lane, supra). The animal's immune response to the immunogen preparation is monitored by taking test bleeds and determining the titer of reactivity to the protein of choice. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-p47ING3 proteins or even other related proteins, e.g., from other organisms, using a competitive binding immunoassay. Specific polyclonal antisera and monoclonal antibodies will usually bind with $K_D$ of at least about 0.1 mM, more usually at least about 1 µM, preferably at least about 0.1 µM or better, and most preferably, 0.01 µM or better.

Once p47ING3 specific antibodies are available, these proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays p47ING3 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case p47ING3, or antigenic fragments thereof). The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled p47ING3 polypeptide or a labeled anti-p47ING3 antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting p47ING3 in samples may be either competitive or noncompetitive. Noncompetitive immunoassays are assays in which the amount of antigen is directly measured. In one preferred "sandwich" assay, for example, the anti-antigen antibodies can be bound directly to a solid substrate on which they are immobilized. These immobilized antibodies then capture antigen present in the test sample. Antigen thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of p47ING3 present in the sample is measured indirectly by measuring the amount of a known, added (exogenous) antigen displaced (competed away) from an anti-antigen antibody by the unknown antigen present in a sample. In one competitive assay, a known amount of antigen is added to a sample and the sample is then contacted with an antibody that specifically binds to the antigen. The amount of exogenous antigen bound to the antibody is inversely proportional to the concentration of antigen present in the sample. In a particularly preferred embodiment, the antibody is immobilized on a solid substrate. The amount of antigen bound to the antibody may be determined either by measuring the amount of antigen present in an antigen/antibody complex, or alternatively by measuring the amount of remaining uncomplexed protein. The amount of antigen may be detected by providing a labeled antigen molecule.

A hapten inhibition assay is another preferred competitive assay. In this assay the known antigen is immobilized on a solid substrate. A known amount of anti-antigen antibody is added to the sample, and the sample is then contacted with the immobilized antigen. The amount of anti-antigen antibody bound to the known immobilized antigen is inversely proportional to the amount of antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, p47ING3 proteins can be immobilized to a solid support. Proteins (e.g., p33ING1 or p33ING2) are added to the assay that compete for binding of the antisera to the immobilized antigen. The ability of the added protein to compete for binding of the antisera to the immobilized protein is compared to the ability of antigen to compete with itself. The percent cross-reactivity for the above proteins is calculated, using standard calculations. Those antisera with less than 10% crossreactivity with the added proteins are selected and pooled. The cross-reacting antibodies are optionally removed from the pooled antisera by immunoabsorption with the added proteins.

The immunoabsorbed and pooled antisera are then used in a competitive binding immunoassay as described above to compare a second protein thought to be perhaps an allele, interspecies homologs, or polymorphic variant of p47ING3, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the first protein that is required to inhibit 50% of binding, then the second protein is said to specifically bind to the polyclonal antibodies generated to the immunogen of choice.

Other Assay Formats

Western blot (immunoblot) analysis is used to detect and quantify the presence of p47ING3 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind p47ING3. The anti-antigen antibodies specifically bind to the antigen on the solid support. These antibodies may be directly labeled or alternatively may be subsequently detected using labeled antibodies (e.g., labeled sheep anti-mouse antibodies) that specifically bind to the anti-antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a specific protein, or secondary antibodies that recognize antibodies to the specific protein.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Measuring Changes in p47ING3 Regulated Cell Growth p47ING3 and its alleles, interspecies homologs, and polymorphic variants participate in regulation of cell proliferation and tumor suppression. Therefore, expression of p47ING3 and its alleles, interspecies homologs, and polymorphic variants in host cells would inhibit cell proliferation and suppress tumor formation. On the other hand, expression of p47ING3 mutants in a cell would lead to abnormal cell proliferation and loss of tumor suppressor phenotypes. Finally, compounds that activate or inhibit p47ING3 would indirectly affect regulation of cellular proliferation and tumor suppression. Any of these changes in cell growth can be assessed by using a variety of in vitro and in vivo assays, e.g., ability to grow on soft agar, changes in contact inhibition and density limitation of growth, changes in growth factor or serum dependence, changes in the level of tumor specific markers, changes in invasiveness into Matrigel, changes in tumor growth in vivo, such as in transgenic mice, etc. Furthermore, these assays can be to screen for activators, inhibitors, and modulators of p47ING3. Such activators, inhibitors, and modulators of p47ING3 can then be used to modulate p47ING3 expression in tumor cells or abnormal proliferative cells.

A. Assays for Changes in Cell Growth by Expression of p47ING3 Constructs

The following are assays that can be used to identify p47ING3 constructs which are capable of regulating cell proliferation and tumor suppression. The phrase "p47ING3 constructs" can refer to any of p47ING3 and its alleles, interspecies homologs, polymorphic variants and mutants. Functional p47ING3 constructs identified by the following assays can then be used in gene therapy to inhibit abnormal cellular proliferation and transformation.

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify p47ING3 constructs, which when expressed in host cells, inhibit abnormal cellular proliferation and transformation. Typically, transformed host cells (e.g., cells that grow on soft agar) are used in this assay. Expression of a tumor suppressor gene in these transformed host cells would reduce or eliminate the host cells' ability to grow in stirred suspension culture or suspended in semi-solid media, such as semi-solid or soft. This is because the host cells would regenerate anchorage dependence of normal cells, and therefore require a solid substrate to grow. Therefore, this assay can be used to identify p47ING3 constructs which function as a tumor suppressor. Once identified, such p47ING3 constructs can be used in gene therapy to inhibit abnormal cellular proliferation and transformation.

Techniques for soft agar growth or colony formation in suspension assays are described in Freshney, *Culture of Animal Cells a Manual of Basic Technique,* 3$^{rd}$ ed., Wiley-Liss, New York (1994), herein incorporated by reference. See also, the methods section of Garkavtsev et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when transfected with tumor suppressor genes, regenerate a normal phenotype and become contact inhibited and would grow to a lower density.

Contact inhibition and density limitation of growth assays can be used to identify p47ING3 constructs which are capable of inhibiting abnormal proliferation and transformation in host cells. Typically, transformed host cells (e.g., cells that are not contact inhibited) are used in this assay. Expression of a tumor suppressor gene in these transformed host cells would result in cells which are contact inhibited and grow to a lower saturation density than the transformed cells. Therefore, this assay can be used to identify p47ING3 constructs which function as a tumor suppressor. Once identified, such p47ING3 constructs can be used in gene therapy to inhibit abnormal cellular proliferation and transformation.

In this assay, labeling index with [$^3$H]-thymidine at saturation density is a preferred method of measuring density limitation of growth. Transformed host cells are transfected with a p47ING3 construct and are grown for 24 hours at saturation density in non-limiting medium conditions. The percentage of cells labeling with [$^3$H]-thymidine is determined autoradiographically. See, Freshney (1994), supra.

The host cells expressing a functional p47ING3 construct would give arise to a lower labeling index compared to control (e.g., transformed host cells transfected with a vector lacking an insert).

Growth Factor or Serum Dependence

Growth factor or serum dependence can be used as an assay to identify functional p47ING3 constructs. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When a tumor suppressor gene is transfected and expressed in these transformed cells, the cells would reacquire serum dependence and would release growth factors at a lower level. Therefore, this assay can be used to identify p47ING3 constructs which function as a tumor suppressor. Growth factor or serum dependence of transformed host cells which are transfected with a p47ING3 construct can be compared with that of control (e.g., transformed host cells which are transfected with a vector without insert). Host cells expressing a functional p47ING3 would exhibit an increase in growth factor and serum dependence compared to control.

Tumor Specific Markers Levels

Tumor cells release an increased amount of certain factors (hereinafter "tumor specific markers") than their normal counterparts. For example, plasminogen activator (PA) is released from human glioma at a higher level than from nounal brain cells (see, e.g., Gullino, *Angiogenesis, tumor vascularization, and potential interference with tumor growth*. In Mihich (ed.): "Biological Responses in Cancer." New York, Academic Press, pp. 178-184 (1985)). Similarly, Tumor angiogenesis factor (TAF) is released at a higher level in tumor cells than their normal counterparts. See, e.g., Folkman, Angiogenesis and cancer, *Sem Cancer Biol*. (1992)).

Tumor specific markers can be assayed for to identify p47ING3 constructs, which when expressed, decrease the level of release of these markers from host cells. Typically, transformed or tumorigenic host cells are used. Expression of a tumor suppressor gene in these host cells would reduce or eliminate the release of tumor specific markers from these cells. Therefore, this assay can be used to identify p47ING3 constructs which function as a tumor suppressor.

Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305-312 (1980); Gulino, *Angiogenesis, tumor vascularization, and potential interference with tumor growth*. In Mihich, E. (ed): "Biological Responses in Cancer." New York, Plenum (1985); Freshney *Anticancer Res.* 5:111-130 (1985).

Invasiveness into Matrigel

The degree of invasiveness into Matrigel or some other extracellular matrix constituent can be used as an assay to identify p47ING3 constructs which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Therefore, functional p47ING3 constructs can be identified by measuring changes in the level of invasiveness between the host cells before and after the introduction of p47ING3 constructs. If a p47ING3 construct functions as a tumor suppressor, its expression in tumorigenic host cells would decrease invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Cell Cycle Analysis

Cell cycle analysis can be used to determine if a gene can suppress the growth of a cell. Briefly, cells are transfected with an expression cassette containing the gene of interest. If the gene encodes a protein that can arrest or inhibit cell division then the gene is suppressing the growth of the cells. Cell division, or mitosis, consists of several successive phases in a eukaryotic cell (*Molecular Biology of the Cell*, 3d edition (Alberts et al., eds., 1994)). These phases, in order, are known as $G_1$, S, $G_2$ and M. DNA replication takes place during the S phase. The mitotic phase, where nuclear division takes place, is termed the M phase. The $G_1$ phase is the time between the M phase and the S phase. $G_2$ is the time between the end of the S phase and the beginning of the M phase. Cells can pause in $G_1$ and enter a specialized resting state known as $G_0$. Cells can remain in $G_0$ for days to years, until they resume the cell-cycle. Methods of analyzing the phase of the cell-cycle are known in the art and include methods that involve determining if the cell is replicating DNA (e.g., [$H^3$]-thymidine incorporation assays). Alternatively, methods are known in the art for measuring the DNA content of a cell, which doubles during the S phase. FACS (Fluorescent activated cell sorting) analysis can be used to determine the percentage of a population of cells in a particular stage of the cell-cycle (see generally, Alberts et al., supra; see also van den Heuvel and Harlow, (1993) *Science* 262: 2050-2054). The cells are incubated with a dye that fluoresces (e.g., propidium iodide) when it binds to the DNA of the cell. Thus, the amount of fluorescence of a cell is proportional to the DNA content of a cell. Cells that are in $G_1$ or $G_0$ ($G_1/G_0$) have an unreplicated complement of DNA and are deemed to have 1 arbitrary unit of DNA in the cell. Those cells that have fully replicated, i.e., have doubled their DNA content, are deemed to have 2 arbitrary units of DNA in the cell and are in the $G_2$ or M phase ($G_2$/M) of the cell cycle. Cells with an amount of DNA that is between 1 and 2 arbitrary units are in S phase.

The effect of a protein of interest on the cell cycle can be determined by transfecting cells with DNA encoding the protein of interest and analyzing its effect on the cell cycle through flow cytometry in a FACS. The cells are co-transfected with a vector encoding a marker to identify and analyze those cells that are actually transfected. Such markers can include the B cell surface marker CD20 (van de Heuvel and Harlow, supra) or a farnesylated green fluorescent protein (GFP-F) (Jiang and Hunter, (1998) *Biotechniques*, 24(3): 349-50, 352, 354).

For example, the percentage of cells in a particular stage of the cell-cycle can be determined using the method of Jiang and Hunter, (1998) supra. Briefly, a population of cells are transfected with a vector encoding p47ING3 and a vector encoding a green fluorescent protein (GFP) with a farnesylation signal sequence from c-Ha-Ras. The farnesylation signal sequence is farnesylated in the cell, which targets the GFP molecule to the plasma membrane. Vectors encoding farnesylated GFP are commercially available (e.g., pEGFP-F from Clontech).

After transfection, the cells are suspended in buffer containing the DNA intercalator propidium iodide. Propidium iodide will fluoresce when it is bound to DNA. Thus, the amount of fluorescence observed from propidium iodide in a FACS flow cytometer is an indication of the DNA content of a cell. The percentages of cells in each cell cycle can be calculated using computer programs, e.g., the ModFit program (Becton-Dickinson). The cell cycle stage of the cell was analyzed after gating cells by GFP fluorescence using FACscan. If the gene encodes a tumor suppressor, the percentage of cells that enter S phase would be decreased, as the cells are arrested in the $G_0/G_1$ phase. Therefore, the percentage of cells that are $G_0/G_1$ phase would be increased.

Tumor Growth In Vivo

Effects of p47ING3 on cell growth can be tested in transgenic or immune-suppressed mice. Knock-out transgenic mice can be made, in which the endogenous p47ING3 gene is disrupted. Such knock-out mice can be used to study effects of p47ING3, e.g., as a cancer model, as a means of assaying in vivo for compounds that modulate p47ING3, and to test the effects of restoring a wildtype p47ING3 to a knock-out mice.

Knock-out transgenic mice can be made by insertion of a marker gene or other heterologous gene into the endogenous p47ING3 gene site in the mouse genome via homologous recombination. Such mice can also be made by substituting the endogenous p47ING3 with a mutated version of p47ING3, or by mutating the endogenous p47ING3, e.g., by exposure to carcinogens.

A DNA construct is introduced into the nuclei of embryonic stem cells.

Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244: 1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

These knock-out mice can be used as hosts to test the effects of various p47ING3 constructs on cell growth. These transgenic mice with the endogenous p47ING3 gene knocked out would develop abnormal cell proliferation and tumor growth. They can be used as hosts to test the effects of various p47ING3 constructs on cell growth. For example, introduction of wildtype p47ING3 into these knock-out mice would inhibit abnormal cellular proliferation and suppress tumor growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. In hosts which developed invasive tumors, cells expressing a p47ING3 construct are injected subcutaneously. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, functional p47ING3 constructs which are capable of inhibiting abnormal cell proliferation can be identified. This model can also be used to identify mutant versions of p47ING3.

B. Assays for Compounds that Modulate p47ING3 p47ING3 and its alleles, interspecies homologs, and polymorphic variants participate in regulation of cell proliferation and tumor suppression. Mutations in these genes, including null or missense mutations, can cause abnormal cell proliferation and tumor growth. The activity of p47ING3 polypeptides (wildtype or mutants) can be assessed using a variety of in vitro and in vivo assays measuring various parameters, e.g., cell growth on soft agar, contact inhibition and density limitation of growth, growth factor or serum dependence, tumor specific markers levels, invasiveness into Matrigel, tumor growth in vivo, transgenic mice, p47ING3 protein or mRNA levels, transcriptional activation or repression of a reporter gene, and the like. Such assays can also be used to screen for activators, inhibitors, and modulators of wildtype and mutant p47ING3. Such activators, inhibitors, and modulators are useful in inhibiting tumor growth and modulating cell proliferation. Compounds identified using the assays of the invention are useful as therapeutics for treatment of cancer and other diseases involving cellular hyperproliferation.

Biologically active or inactivated p47ING3 polypeptides, either recombinants or naturally occurring, are used to screen activators, inhibitors, or modulators of tumor suppression and cell proliferation. The p47ING3 polypeptides can be recombinantly expressed in a cell, naturally expressed in a cell, recombinantly or naturally expressed in cells transplanted into an animal, or recombinantly or naturally expressed in a transgenic animal. Modulation is tested using one of the in vitro or in vivo assays described in herein in part A.

Cells that have wildtype p47ING3 are used in the assays of the invention, both in vitro and in vivo. Preferably, human cells are used. Cell lines can also be created or isolated from tumors that have mutant p47ING3. Optionally, the cells can be transfected with an exogenous p47ING3 gene operably linked to a constitutive promoter, to provide higher levels of p47ING3 expression. Alternatively, endogenous p47ING3 levels can be examined. The cells can be treated to induce p47ING3 expression. The cells can be immobilized, be in solution, be injected into an animal, or be naturally occurring in a transgenic or non-transgenic animal.

Samples or assays that are treated with a test compound which potentially activates, inhibits, or modulates p47ING3 are compared to control samples that are not treated with the test compound, to examine the extent of modulation. Generally, the compounds to be tested are present in the range from 0.1 nM to 10 mM. Control samples (untreated with activators, inhibitors, or modulators) are assigned relative p47ING3 activity value of 100%. Inhibition of p47ING3 is achieved when the p47ING3 activity value relative to the control is about 90% (e.g., 10% less than the control), preferably 50%, more preferably 25%. Activation of p47ING3 is achieved when the p47ING3 activity value relative to the control is 110% (e.g., 10% more than the control), more preferably 150%, more preferably 200% higher.

The effects of the test compounds upon the function of the p47ING3 polypeptides can be measured by examining any of the parameters described above. For example, parameters such as ability to grow on soft agar, contact inhibition and density limitation of growth, growth factor or serum dependence, tumor specific markers levels, invasiveness into Matrigel, tumor growth in vivo, transgenic mice and the like, can be measured. Furthermore, the effects of the test compounds on p47ING3 protein or mRNA levels, transcriptional activation or repression of a reporter gene can be measured. In each assay, cells expressing p47ING3 are contacted with a test compound and incubated for a suitable amount of time, e.g., from 0.5 to 48 hours. Then, parameters such as those described above are compared to those produced by control cells untreated with the test compound.

In one embodiment, the effect of test compounds upon the function of p47ING3 can be determined by comparing the level of p47ING3 protein or mRNA in treated samples and control samples. The level of p47ING3 protein is measured using immunoassays such as western blotting, ELISA and the like with a p47ING3 specific antibody. For measurement of mRNA, amplification, e.g., using PCR, LCR, or hybridization assays, e.g., northern hybridization, RNase protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the p47ING3 promoter operably linked to a reporter gene such as luciferase, green fluorescent protein, CAT, or β-gal. After treatment with a potential p47ING3 modulator, the amount of reporter gene transcription, translation, or activity is measured according to standard techniques known to those of skill in the art.

In another embodiment, the effects of test compounds on p47ING3 activity is performed in vivo. In this assay, cultured cells that are expressing a wildtype or mutant p47ING3 (e.g., a null or missense mutation) are injected subcutaneously into an immune compromised mouse such as an athymic mouse, an irradiated mouse, or a SCID mouse. The p47ING3 modulators are administered to the mouse, e.g., a chemical ligand library. After a suitable length of time, preferably 4-8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Alternatively, transgenic mice with the endogenous p47ING3 gene knocked out can be used in an assay to screen for compounds which modulate the p47ING3 activity. As described in part A, knock-out transgenic mice can be made, in which the endogenous p47ING3 gene is disrupted, e.g., by replacing it with a marker gene. A transgenic mouse that is heterozygous or homozygous for integrated transgenes that have functionally disrupted the endogenous p47ING3 gene can be used as a sensitive in vivo screening assay for p47ING3 ligands and modulators of p47ING3 activity.

C. Modulators

The compounds tested as modulators of p47ING3 can be any small chemical compound, or a biological entity, such as a protein, sugar, nucleic acid or lipid. Alternatively, modulators can be genetically altered versions of p47ING3. For example, an antisense construct of p47ING3 can be used as a modulator.

Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel et al, supra, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing p47ING3 is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay several different plates per day; assay screens for up to about 6,000-20,000 different compounds is possible using the integrated systems of the invention. More recently, microfluidic approaches to reagent manipulation have been developed, e.g., by Caliper Technologies (Palo Alto, Calif.).

D. Computer-Based Assays

Yet another assay for compounds that modulate p47ING3 activity involves computer assisted drug design, in which a computer system is used to generate a three-dimensional structure of p47ING3 based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering p47ING3 amino acid sequences of at least 10 amino acid residues or corresponding nucleic acid sequences encoding a p47ING3 polypeptide into the computer system. The amino acid sequence of the polypeptide or the nucleic acid encoding the polypeptide is selected from the group consisting of SEQ ID NO:1 or SEQ ID NO:2, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art. The three-dimensional structural model of the protein can be saved to a computer readable form and be used for further analysis (e.g., identifying potential ligand binding regions of the protein and screening for mutations, alleles and interspecies homologs of the gene).

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the p47ING3 protein to identify ligands that bind to p47ING3. Binding affinity between the protein and ligands is determined using energy turns to determine which ligands have an enhanced probability of binding to the protein. The results, such as three-dimensional structures for potential ligands and binding affinity of ligands, can also be saved to a computer readable form and can be used for further analysis (e.g., generating a three dimensional model of mutated proteins having an altered binding affinity for a ligand).

Computer systems are also used to screen for mutations, polymorphic variants, alleles and interspecies homologs of p47ING3 genes. Such mutations can be associated with disease states or genetic traits. As described above, high density oligonucleotide arrays (GeneChip™) and related technology can also be used to screen for mutations, polymorphic variants, alleles and interspecies homologs. Once the variants are identified, diagnostic assays can be used to identify patients having such mutated genes. Identification of the mutated p47ING3 genes involves receiving input of a first nucleic acid or amino acid sequence encoding selected from the group consisting of SEQ ID NO:2, or SEQ ID NO:1, and conservatively modified versions thereof. The sequence is entered into the computer system as described above and then saved to a computer readable form. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in p47ING3 genes, and mutations associated with disease states and genetic traits.

VII. Gene Therapy

The present invention provides the nucleic acids of p47ING3 for the transfection of cells in vitro and in vivo. These nucleic acids can be inserted into any of a number of well known vectors for the transfection of target cells and organisms as described below. The nucleic acids are transfected into cells, ex vivo or in vivo, through the interaction of the vector and the target cell. The nucleic acids encoding p47ING3, under the control of a promoter, then expresses a p47ING3 of the present invention, thereby mitigating the effects of absent, partial inactivation, or abnormal expression of the p47ING3 gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Mulligan, *Science* 926-932 (1993); Dillon, *TIBTECH* 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1:13-26 (1994)).

Delivery of the gene or genetic material into the cell is the first critical step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389

(1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *Proc. Natl. Acad. Sci. U.S.A.* 81:6466-6470 (1984); and Samulski et al., *J. Virol.* 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *Proc. Natl. Acad. Sci. U.S.A.* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et at, *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic nucleic acids can be also administered directly to the organism for transduction of cells in vivo. Alternatively, naked DNA can be administered.

Administration is by any of the routes normally used for introducing a molecule into ultimate contact with blood or tissue cells, as described below. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route (see *Proc. Natl. Acad. Sci. U.S.A.* 81:6466-6470 (1984); and Samulski et al., *J. Virol.* 63:03822-3828 (1989)). In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

VIII. Pharmaceutical Compositions and Administration p47ING3 nucleic acid, protein, and modulators of p47ING3 can be administered directly to the patient for inhibition of cancer, tumor, or precancer cells in vivo. Administration is by any of the routes normally used for introducing a compound into ultimate contact with the tissue to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The compounds (nucleic acids, proteins, and modulators), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient, in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient In determining the effective amount of the modulator to be administered in the treatment or prophylaxis of cancer, the physician evaluates circulating plasma levels of the modulator, modulator toxicities, progression of the disease, and the production of anti-modulator antibodies. In general, the dose equivalent of a modulator is from about 1 ng/kg to 10 mg/kg for a typical patient. Administration of compounds is well known to those of skill in the art (see, e.g., Bansinath et al., *Neurochem Res.* 18:1063-1066 (1993); Iwasaki et al., *Jpn. J. Cancer Res.* 88:861-866 (1997); Tabrizi-Rad et al., *Br. J. Pharmacol.* 111:394-396 (1994)).

For administration, modulators of the present invention can be administered at a rate determined by the LD-50 of the modulator, and the side-effects of the inhibitor at various concentrations, as applied to the mass and overall health of the patient. Administration can be accomplished via single or divided doses.

IX. Diagnostics and Kits

The present invention also provides methods for detection of p47ING3 (either wildtype or mutant). For example, kits are provided that contain p47ING3 specific reagents that specifically hybridize to p47ING3 nucleic acid, such as specific probes and primers, and p47ING3 specific reagents that specifically bind to the protein of choice, e.g., antibodies. The methods, kits, and the assays described herein can be used for identification of modulators of p47ING3, or for diagnosing patients with mutations in p47ING3.

Nucleic acid assays for the presence of p47ING3 DNA and RNA in a sample include numerous techniques are known to those skilled in the art. In particular, p47ING3 specific reagents (e.g., p47ING3-specific primers or nucleic acid probes) can be used to distinguish between samples which contain p47ING3 nucleic acids and samples which contain p33ING1 or p33ING2 nucleic acids. Techniques such as Southern analysis, Northern analysis, dot blots, RNase protection, high density oligonucleotide arrays, Si analysis, amplification techniques such as PCR and LCR, and in situ hybridization can be used as assays. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987).

In addition, p47ING3 protein can be detected with the various immunoassay techniques described above, e.g., ELISA, Western blotting, and the like. The test sample is typically compared to both a positive control (e.g., a sample expressing recombinant p47ING3) and a negative control. In particular, p47ING3, p33ING1 or p33ING2 specific polyclonal and monoclonal antibodies or specific polyclonal and monoclonal antibodies can be used as a diagnostic tool to distinguish between samples which contain p47ING3, p33ING1, or p33ING2 antigens.

The present invention also provides for kits for screening for modulators of p47ING3. Such kits can be prepared from readily available materials and reagents. For example, such kits can comprise any one or more of the following materials: p47ING3, reaction tubes, and instructions for testing p47ING3 activity. Preferably, the kit contains biologically active p47ING3. A wide variety of kits and components can be prepared according to the present invention, depending upon the intended user of the kit and the particular needs of the user.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example I

Cloning and Expression of p47ING3 p47ING3 homologous sequences were found in a random cDNA sequence database consisting of short partial sequences known as expressed sequence tags (ESTs) submitted in GenBank. Using primers designed based on these EST sequences and using RT-PCR and 5'- and 3'-RACE methods, p47ING3 coding region (SEQ ID NO:2) from human placenta cDNA (CLONTECH) was isolated and subcloned into a plasmid. The amino acid sequence of p47ING3 (SEQ ID NO: 1) has about 34% amino acid identity with p33ING1 (SEQ ID NO: 8 (p33ING1)) and p33ING2 (SEQ ID NO: 6 (p33ING2).

Example II

Antibodies to p47ING3 Against Interior Peptide Sequence

Antibodies to p47ING3 were synthesized against the peptide ping-3 from p47ING3 (SEQ ID NO:5: HTPVEKRKYNPTSHHTT). The peptide is amino acids 141-157 of SEQ ID NO: 1. The peptide was purified by HPLC; peptide KLH conjugations were made; and rabbits were immunized by them. Antiserum was purified using peptide affinity column and specificity of each polyclonal antibody was analyzed by ELISA.

p33ING1, p33ING2, and p47ING3 proteins were produced by Promega's TNT Quick Coupled Transcription/Translation System (Rabbit Reticulocyte Lysate) from pcDNA3.1-ING1, ING2, and ING3 expression vectors.

Plasmids encoding p33ING1, p33ING2, and p47ING3 were separately subjected to an in vitro transcription/translation system to produce the respective proteins. The proteins were electrophoresed on SDS-PAGE and Western blotted. The blot was incubated with anti-p47ING3 polyclonal antibodies and detection was performed using a horse radish peroxidase labelled system from Amersham Pharmacia Biotech. As shown in FIG. 1, anti-p47ING3 polyclonal antibodies are reactive with recombinant p47ING3 protein, but are not cross-reactive with recombinant p33ING1 protein or recombinant p33ING2 protein. The p47ING3 protein migrates an a size appropriate for its predicted molecular weight of 47 kDa.

Example III

Antibodies to p47ING3 Against N-Terminal Sequence

Antibodies to p47ING3 were synthesized against the peptide Ping-3N from p47ING3 (SEQ ID NO:9: MLYLE- DYLEM; amino acids 1-10 of SEQ ID NO: 1). The peptide was purified by HPLC; peptide KLH conjugations were made; and rabbits were immunized by them. Antiserum was purified using peptide affinity column and specificity of each polyclonal antibody was analyzed by ELISA and Western blot analysis.

p33ING1, p33ING2, and p47ING3 proteins were produced by Promega's TNT Quick Coupled Transcription/Translation System (Rabbit Reticulocyte Lysate) from pcDNA3.1-ING1, ING2, and ING3 expression vectors.

Plasmids encoding p33ING1, p33ING2, and p47ING3 were separately subjected to an in vitro transcription/translation system to produce the respective proteins. The proteins were electrophoresed on SDS-PAGE with molecular weight markers (Kaleidoscope Prestained Standards; Bio-Rad; 161-0324) and Western blotted to a Immobilon-P membrane (Millipore, IPVH15150). The blot was incubated with anti-p47ING3 polyclonal antibodies (1:200 dilution) and detection was performed using a secondary antibody—goat anti-rabbit IgG HRP conjugate (Santa Cruz Biotechnology, sc-2004) (1:2000 dilution). Detection was carried out using ECL Western Blotting Detection Reagents (Amersham Pharmacia Biotech, RPN2106) and Hyperfilm ECL (Amersham Pharmacia Biotech, RPN2103K). The autoradiogram of the Western blot is depicted as FIG. 2.

Figure 2:
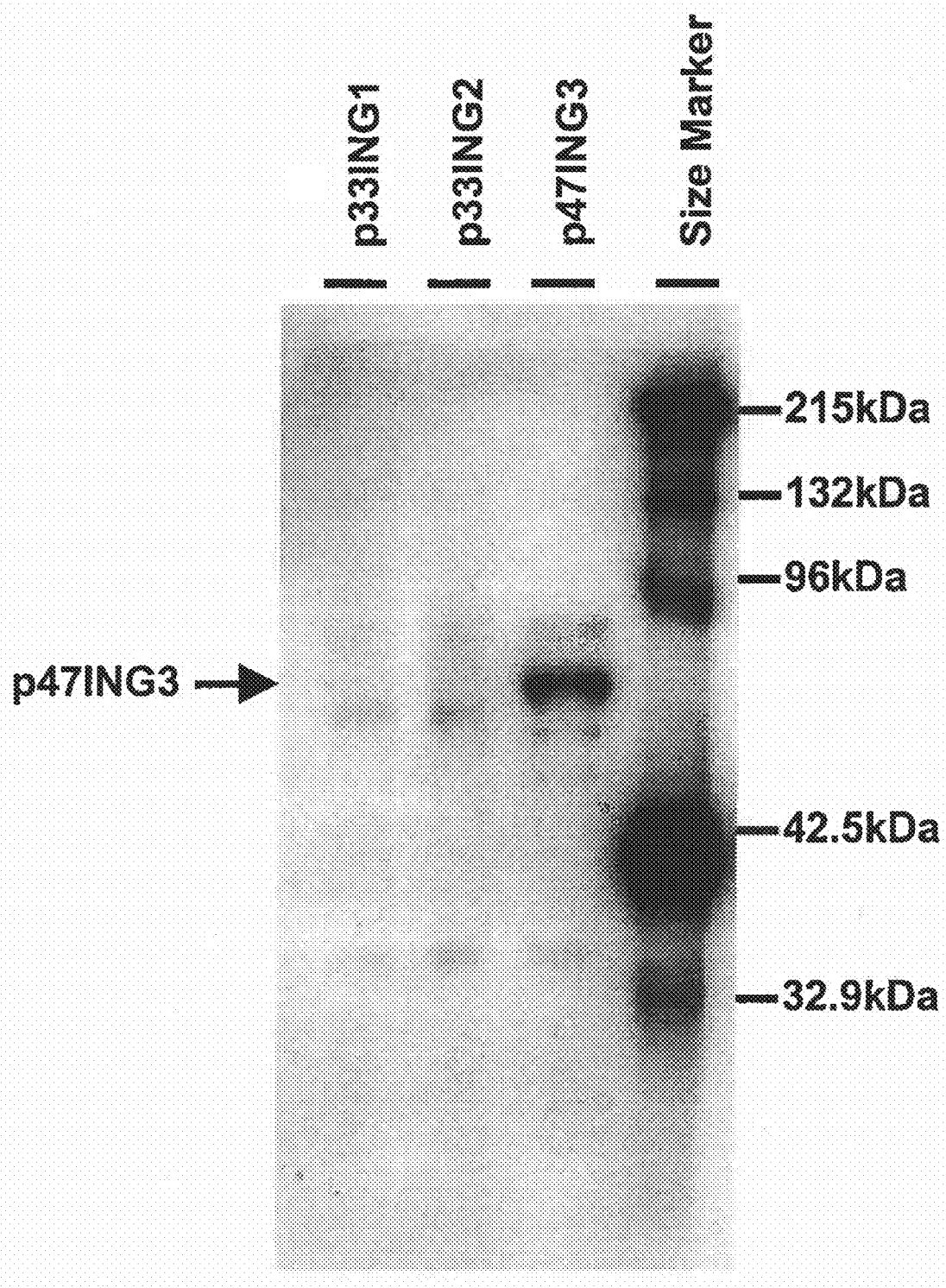
FIG. 2 illustrates binding specificities of polyclonal antibodies for p47ING3 raised against SEQ ID NO: 9 by Western blot analysis. The molecular sizes of standards are indicated in kDa on the right hand border of FIG. 2. The proteins were produced using the TNT T7 Quick Coupled Transcription/Translation System, Cat. #L1170 from Promega Corporation of Madison, Wis. The proteins were electrophoresed and Western blotted. The Western blot was incubated with an anti-p47ING3 antibody (diluted 1:200) raised against SEQ ID NO: 9. The presence of the p47ING3 immunoreactive bands was visualized with a goat anti-rabbit IgG-HRP (1:2000 dilution) (Santa Cruz Biotechnology) and ECL Western Blotting Detection Reagents (Amersham Pharmacia Biotech, RPN2106). The blot was then subjected to autoradiography using Hyperfilm ECL (Amersham Pharmacia Biotech, RPN2103K).

As shown in FIG. 2, anti-p47ING3 polyclonal antibodies are reactive with recombinant p47ING3 protein, but are not cross-reactive with recombinant p33ING1 protein or recombinant p33ING2 protein. The immunoreactive band in the p47ING3 lane protein migrates an a size appropriate for the predicted molecular weight of p47ING3 of 47 kDa.

Example IV

Inhibition of Cell Proliferation

Figure 3:
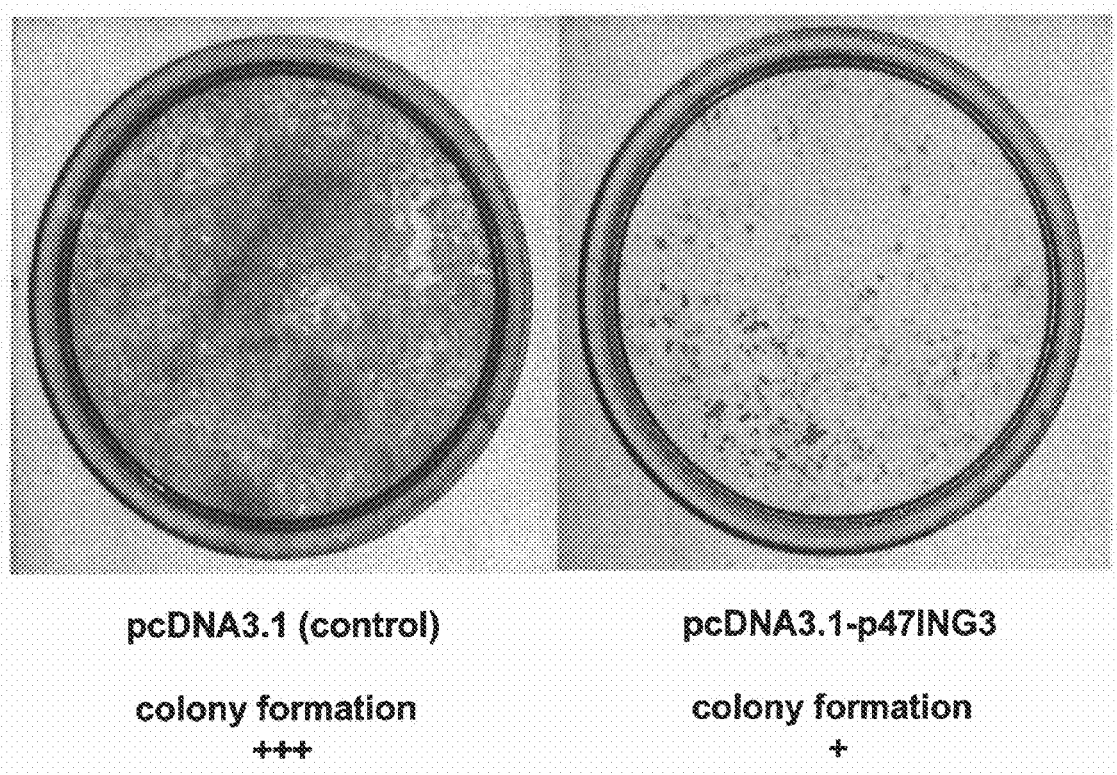
FIG. 3 illustrates that p47ING3 inhibits the cell growth of the human colon carcinoma RKO cell line by colony formation assay. The left hand panel shows RKO cells transfected with the parent vector pcDNA3.1 and the right hand panel shows RKO cells transfected with a vector that encodes for p47ING3, pcDNA3.1-p47ING3.

The colony formation assay was used to determine if p47ING3 inhibits cell growth of the RKO human colon carcinoma cell line which is available from the ATCC. A mammalian expression vector (with CMV promoter, Neomycin resistant) containing p47ING3 in the sense orientation (pcDNA3.1-p47ING3) was constructed in the expression vector pcDNA3.1 (Invitrogen). RKO cell lines were transfected with the parent vector pcDNA3.1 or with pcDNA3.1-p47ING3. The transfected cells were selected with G418 to clone those cells with neomycin resistance. The RKO (pcDNA3.1) and the RKO (pcDNA3.1-p47ING3) cell lines were subjected to the colony formation assay was analyze the effect of p47ING3 on cellular proliferation. As shown in FIG. 3, RKO cells transfected with pcDNA3.1-p47ING3 formed less colonies compared to RKO cells transfected with pcDNA3.1. This result illustrates that p47ING3 can inhibit cell growth.

Example V

Cell Cycle Assay of p47ING3 Transfected Cells

Cell-cycle stage analysis of cells transfected with an expression vector encoding p47ING3 was performed using the method of Jiang and Hunter, supra. The method permits the analysis of cell-cycle profiles in transfected cells using a membrane-targeted green fluorescent protein (GFP).

RKO cells were plated in a 50 cm$^2$ dish at a density of $1\times10^4$ cells/cm$^2$. Plasmid DNA mixtures that contained 0.15 picomoles of pEGFP-F Amp with either 0.015 picomoles of pcDNA3.1 (Invitrogen) or 0.015 picomoles of pcDNA3.1-p47ING3 were transfected using LipofectAMINE reagent (Life Technologies). Vector pEGFP-F Amp (ampicillin resistant) was constructed from vector from peGFP-F by replacing the kanamycin resistance gene with an ampicillin resistance gene. Vector pEGFP-F is available for Clontech and is kanamycin resistant.

After 3 hours of incubation, the medium was changed to fresh DMEM with 10% FBS. After an additional 48 hour incubation, the cells were harvested, fixed in 70% ethanol and then suspended in PBS containing 20 µg/ml propidium iodide and 100 µg/ml RNaseA. The propidium iodide signal was used as a measure for DNA content to determine cell-cycle profiles on a FACScan flow cytometer (Becton-Dickinson). The cell cycle stage of the cell was analyzed after gating cells by GFP fluorescence using FACscan. Cells with a green fluorescent signal at least 2 times stronger than that in the negative cells are considered GFP-positive and cells with a signal equal to or less than negatives cells are considered GFP-negative. Those cells exhibiting a green fluorescent signal at least 2 times stronger than that in the negative cells were considered GFP-positive and cells with a signal equal to or less than negatives cells were considered GFP-negative. The percentages of the cells in each cell cycle phase (($G_0/G_1$), S and ($G_2/M$)) were calculated by the ModFit program (Becton-Dickinson) (FIG. 4). The cell-cycle profiles of GFP-positive and GFP-negative populations from the same dish can be compared. Typically, each DNA histogram contains data from at least 10,000 cells. In this experiment, the RKO cells transfected with pcDNA3.1-p47ING3 have 13.4% more cells in the $G_0/G_1$ phase as compared to RKO cells transfected with pcDNA3.1 (FIG. 4). The percentage of RKO (pcDNA3.1) cells in the S and $G_2/M$ phases is higher than RKO (pcDNA3.1-p47ING3) cells. This indicates that p47ING3 is able to increase the number of cells in the $G_0/G_1$ phase. Therefore, it appears that p47ING3 is able to induce cell cycle arrest at G0/G1 phase and decrease the number of RKO cells that are entering S phase (DNA synthesis).

Example VI

Soft Agar Assay for Identifying Compounds that Modulate p47ING3

Wildtype or mutant p47ING3 is expressed in host cells to screen compounds that modulate anchorage dependence of host cells expressing p47ING3. This is achieved by using the method disclosed in Garkavtsev et al. (1996), supra, herein incorporated by reference. NMuMG cells are transfected with retrovirus produced from a vector containing p47ING3 in sense or antisense orientation, or a vector lacking insert (control). The soft agar culture is comprised of two layers: an underlay (DMEM, 10% FCS, 0.6% agar) and an overlay (DMEM, 10% FCS, 0.3% agar), $5\times10^4$ cells are plated in soft agar in 10 cm plates are left at 37° C. for 6-7 weeks before being counted. The cells are incubated with a test compound for a suitable amount of time, e.g., for 0.5 to 48 hours, before counting cells. The amount of cells in the test sample is then compared to control cells untreated with the compound.

All publications, patents, and patent applications cited herein are hereby incorporated by reference in their entirety for all purposes.

What is claimed is:

1. An isolated nucleic acid encoding a polypeptide p47ING3, wherein the nucleic acid encodes a polypeptide comprising (i) an amino acid sequence having at least 95% identity to SEQ ID NO:1 and (ii) the amino acid sequence of SEQ ID NO:9.

2. The isolated nucleic acid of claim 1, wherein the polypeptide comprises the amino acid sequence of SEQ ID NO:1.

3. The isolated nucleic acid of claim 1, wherein the nucleic acid comprises the nucleotide sequence of SEQ ID NO: 2.

4. An isolated expression vector comprising the nucleic acid of claim 1.

5. A isolated host cell transfected with the vector of claim 4.

* * * * *